United States Patent [19]

Barnes et al.

[11] Patent Number: 5,284,863
[45] Date of Patent: Feb. 8, 1994

[54] HALOALKYLTHIO, -SULFINYL AND -SULFONYL ARYLPYRROLE FUNGICIDAL AGENTS

[75] Inventors: Keith D. Barnes, Newtown, Pa.; Victor M. Kamhi, Hamilton, N.J.; Robert E. Diehl, Yardley, Pa.

[73] Assignee: American Cyanamid Company, Wayne, N.J.

[21] Appl. No.: 803,294

[22] Filed: Dec. 4, 1991

[51] Int. Cl.$^5$ .................... A01N 55/00; A01N 57/60; A01N 43/36

[52] U.S. Cl. ...................... 514/427; 514/63; 514/91; 514/426

[58] Field of Search .................. 514/426, 427, 63, 91

[56] References Cited

U.S. PATENT DOCUMENTS 4,267,184 5/1981 Cherkofsky .................. 514/424

*Primary Examiner*—Allen J. Robinson
*Attorney, Agent, or Firm*—Michael P. Morris

[57] ABSTRACT

Haloalkylthio, -sulfinyl and -sulfonyl arylpyrrole compounds which are effective for the phytopathogenic fungi are described. A method for the fungicidal use of said compounds and methods for the preparation of said compounds are presented.

9 Claims, No Drawings

HALOALKYLTHIO, -SULFINYL AND -SULFONYL ARYLPYRROLE FUNGICIDAL AGENTS

BACKGROUND OF THE INVENTION

Substituted arylpyrroles and their use as insecticidal agents are described in co-pending U.S. patent application Ser. No. 07/392,495 filed on Aug. 11, 1989, now abandoned, and in co-pending U.S. patent application Ser. Nos. 07/803,289, 07/803,295 and 07/804,260, all filed concurrently herewith on Dec. 4, 1991. None of the arylpyrroles disclosed in that patent application are within the scope of the present invention.

It is an object of the present invention to provide haloalkylthio, -sulfinyl and -sulfonyl arylpyrrole compounds that are highly effective for controlling fungi. It is also an object of the invention to protect growing and harvested crops from attack or infestation by phytopathogenic fungi.

These and other objectives of the invention will become more apparent from the detailed description thereof set forth below.

SUMMARY OF THE INVENTION

The present invention describes haloalkylthio, -sulfonyl and -sulfonyl arylpyrole compounds and compositions that are highly effective fungicidal agents useful for protecting agronomic crops from the ravages of phytopathogenic fungi.

The haloalkylthio, -sulfinyl and -sulfonyl arylpyrole compounds of the present invention have the structural formula I $$\text{(I)}$$

[structure showing pyrrole ring with substituents X, Y, Z, W, R]

wherein

W is $S(O)_nCF_2R_1$;

$R_1$ is H, F, Cl, Br, $CF_2H$, $CCl_2H$, $CClFH$, $CF_3$ or $CCl_3$;

n is an integer of 0, 1 or 2;

X is phenyl optionally substituted with one to three halogen, $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, CN, $NO_2$, $CF_3$, $R_2CF_2B$, $R_3CO$ or $NR_4R_5$ groups;

B is $S(O)_n$ or O;

$R_2$ is H, F, $CF_2H$, $CClFH$ or $CF_3$;

$R_3$ is $C_1$-$C_3$ alkyl, $C_1$-$C_3$ alkoxy or $NR_4R_5$;

$R_4$ is H or $C_1$-$C_3$ alkyl;

$R_5$ is H or $C_1$-$C_3$ alkyl or $R_6CO$;

$R_6$ is H or $C_1$-$C_3$ alkyl;

Y is H, halogen, $CF_3$, CN, $NO_2$, $S(O)_nCF_2R_1$ or phenyl optionally substituted with one to three halogen, $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, CN, $NO_2$, $CF_3$, $R_2CF_2B$, $R_3CO$ or $NR_4R_5$ groups;

Z is H, halogen or $CF_3$;

R is H, CN, $$\overset{O}{\underset{}{\|}}CR_7, \quad \overset{O}{\underset{}{\|}}R_8CHNHCR_9, \quad CH_2SQ,$$

$C_1$-$C_6$ alkyl optionally substituted with one to three halogen atoms,
one tri($C_1$-$C_4$ alkyl)silyl,
one hydroxy,
one cyano,
one or two $C_1$-$C_4$ alkoxy groups optionally substituted with one to three halogen atoms,
one $C_1$-$C_4$ alkylthio,
one phenyl optionally substituted with one to three halogen atoms, one to three $C_1$-$C_4$ alkyl groups or one to three $C_1$-$C_4$ alkoxy groups,
one phenoxy group optionally substituted with one to three halogen atoms, one to three $C_1$-$C_4$ alkyl groups or one to three $C_1$-$C_4$ alkoxy groups,
one benzyloxy group optionally substituted on the phenyl ring with one to three halogen atoms, one to three $C_1$-$C_4$ alkyl groups or one to three $C_1$-$C_4$ alkoxy groups,
one $C_1$-$C_6$ alkylcarbonyloxy group optionally substituted with one to three halogen atoms,
one $C_2$-$C_6$ alkenylcarbonyloxy group optionally substituted with one to three halogen atoms,
one phenylcarbonyloxy group optionally substituted with one to three halogen atoms, one to three $C_1$-$C_4$ alkyl groups or one to three $C_1$-$C_4$ alkoxy groups,
one $C_1$-$C_6$ alkoxycarbonyl group optionally substituted with one to three halogen atoms or one to three $C_1$-$C_4$ alkoxy groups,
one benzylcarbonyloxy group optionally substituted on the phenyl ring with one to three halogen atoms, one to three $C_1$-$C_4$ alkyl groups or one to three $C_1$-$C_4$ alkoxy groups, or
one 2-furylcarbonyloxy group,
$C_3$-$C_6$ alkenyl optionally substituted with one to three halogen atoms or one phenyl group, or
$C_3$-$C_6$ alkynyl optionally substituted with one to three halogen atoms or one phenyl group;

$R_7$ is $C_1$-$C_6$ alkyl or $C_3$-$C_6$ cycloalkyl each optionally substituted with
one to three halogen atoms,
one hydroxy,
one cyano,
one or two $C_1$-$C_4$ alkoxy groups optionally substituted with one to three halogen atoms,
one $C_1$-$C_4$ alkylthio,
one phenyl group optionally substituted with one to three halogen atoms, one to three $C_1$-$C_4$ alkyl groups or one to three $C_1$-$C_4$ alkoxy groups,
one phenoxy group optionally substituted with one to three halogen atoms, one to three $C_1$-$C_4$ alkyl groups or one to three $C_1$-$C_4$ alkoxy groups,
one benzyloxy group optionally substituted on the phenyl ring with one to three halogen atoms, one to three $C_1$-$C_4$ alkyl groups or one to three $C_1$-$C_4$ alkoxy groups,
one $C_1$-$C_6$ alkyl carbonyloxy group optionally substituted with one to three halogen atoms,
one $C_2$-$C_6$ alkenylcarbonyloxy group optionally substituted with one to three halogen atoms,
one phenylcarbonyloxy group optionally substituted with one to three halogen atoms, one to three $C_1$-$C_4$ alkyl groups or one to three $C_1$-$C_4$ alkoxy groups,
one $C_1$-$C_6$ alkoxycarbonyl group optionally substituted with one to three halogen atoms, or one to three $C_1$-$C_4$ alkyoxy groups, or one benzyloxycarbonyl group optionally substituted one the phenyl ring with one to three halogen atoms, one to three $C_1$–$C_4$ alkyl groups or one to three $C_1$–$C_4$ alkoxy groups, $C_2$–$C_6$ alkenyl optionally substituted with one to three halogen atoms or one phenyl group, $C_3$–$C_6$ alkynyl optionally substituted with one to three halogen atoms or one phenyl group, phenyl optionally substituted with one to three halogen atoms, one to three $C_1$–$C_4$ alkyl groups, one $C_5$–$C_{12}$ alkyl group, one to two $C_1$–$C_4$ alkoxy groups, or one phenoxy, $C_1$–$C_4$ alkylthio, trialkylsilyl, $C_1$–$C_4$ alkylsulfinyl, $C_1$–$C_4$ alkylsulfonyl, carbo-$C_1$–$C_4$-alkoxy, carboxy, $CF_3$, CN, $NO_2$, di($C_1$–$C_4$ alkyl) amino, $R_2CF_2B$ or $C_1$–$C_4$ alkanoylamino, phenoxy optionally substituted with one to three halogen atoms, one or two $C_1$–$C_4$ alkyl groups, one or two $C_1$–$C_4$ alkoxy groups, trialkylsilyl, $CF_3$, CN, $NO_2$, or di($C_1$–$C_4$ alkyl)amino groups, or $C_1$–$C_4$ alkanoylamino, 1- or 2-naphthyl, 2-, 3-, or 4-pyridyl optionally substituted with one to three halogen atoms, a heteroaromatic 5-membered ring containing an oxygen, nitrogen, or a sulfur atom, and optionally substituted with one to three halogen atoms, $C_1$–$C_6$ alkoxy group optionally substituted with one to three halogen atoms; or $C_2$–$C_6$ alkenyloxy group optionally substituted with one to three halogen atoms;

$R_8$ is hydrogen or $C_1$–$C_4$ alkyl;

$R_9$ is $C_1$–$C_6$ alkyl optionally substituted with one to three halogen atoms, phenyl optionally substituted with one or two halogen, CN, $NO_2$, $C_1$–$C_4$ alkyl, $C_1$–$C_4$ alkoxy or $CF_3$ groups, 2- or 3-thienyl or 2- or 3-furyl;

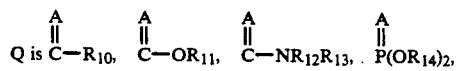

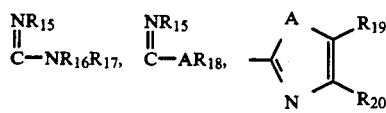

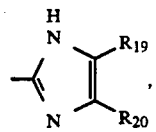

CN, $C_1$–$C_6$ alkyl optionally substituted with one or more phenyl, CN or halogen groups or phenyl optionally substituted with one to three $C_1$–$C_3$ alkyl, $C_1$–$C_3$ alkoxy, halogen, CN, $NO_2$, $CF_3$ or $NR_{21}R_{22}$ groups;

A is O or S;

$R_{10}$ is $C_1$–$C_6$ alkyl or phenyl;

$R_{11}$ is $C_1$–$C_6$ alkyl;

$R_{12}$ and $R_{13}$ are each independently hydrogen, $C_1$–$C_6$ alkyl or may be taken together with the atom to which they are attached to form a 5- to 7- membered ring;

$R_{14}$ is $C_1$–$C_4$ alkyl;

$R_{15}$ is hydrogen, $C_1$–$C_4$ alkyl or may be taken together with either $R_{16}$ or $R_{18}$ and the atoms to which they are attached to form a 5- to 7-membered ring optionally substituted with one or two $C_1$–$C_3$ alkyl groups;

$R_{16}$ and $R_{17}$ are each independently hydrogen or $C_1$–$C_4$ alkyl;

$R_{18}$ is $C_1$–$C_4$ alkyl or when taken together with $R_{15}$ and the atoms to which they are attached may form a 5- to 7- membered ring optionally substituted with one or two $C_1$–$C_3$ alkyl groups;

$R_{19}$ and $R_{20}$ are each independently hydrogen or $C_1$–$C_3$ alkyl or when taken together may form a ring wherein $R_{19}R_{20}$ is represented by —C=C—C=C—; and $R_{21}$ and $R_{22}$ are each independently hydrogen or $C_1$–$C_3$ alkyl.

By the term halogen we intend an atom selected from the group consisting of F, Cl, Br and I.

DETAILED DESCRIPTION OF THE INVENTION

The haloalkylthio, -sulfinyl and -sulfonyl arylpyrrole compounds of the present invention are useful in the control or prevention of phytopathogenic fungi, the causal agents for diseases infecting agronomic crops, both growing and harvested. Preferred haloalkylthio, -sulfinyl and -sulfonyl arylpyrrole fungicidal agents have the structural formula II

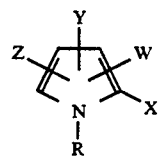

(II)

wherein

W is $S(O)_nCF_2R_1$;

X is phenyl substituted with one to three halogen, CN, $NO_2$, $CF_3$ or $R_2CF_2B$ groups;

Y is H, Cl, Br, $CF_3$, CN or $S(O)_nCF_2R_1$;

Z is H, Cl, Br or $CF_3$;

R is H or $C_1$–$C_4$ alkyl optionally substituted with one to three halogen atoms, one $C_1$–$C_4$ alkoxy group, one cyano, one $C_1$–$C_6$ alkylcarbonyloxy group, one phenylcarbonyloxy group optionally substituted with one to three halogen atoms or one $C_1$–$C_4$ alkyl group, one benzylcarbonyloxy group or one 2-furylcarbonyloxy group; and $R_2$ and $R_2$ are as described above.

Preferred formula II compounds especially useful in the control or prevention of phytopathogenic fungi are illustrated by formula III and formula IV

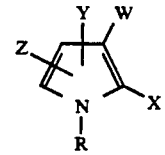

(III)

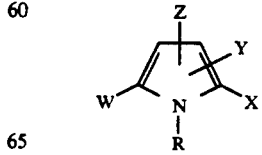

(IV)

wherein

W is $SO_2CF_3$;

X is phenyl substituted with one or two halogen, $C_1-C_3$ alkyl or $CF_3$ groups;

Y is H, Cl, Br, $CF_3$ or CN;

Z is H, Cl or Br and

R is H or $C_1-C_4$ alkyl substituted with one $C_1-C_4$ alkoxy group.

Certain haloalkylsulfonyl arylpyrrole compounds of formula I, wherein W is $SO_2CF$ Y, Z and R are H, and X and $R_1$ are as described above for formula I, may be prepared by reacting an arylethynyl haloalkylsulfonyl compound of formula V $$X-C\equiv C-SO_2CF_2R_1 \qquad (V)$$

wherein X and $R_1$ are as described above with at least one molar equivalent of an aminoacetaldehyde di($C_1-C_4$ alkyl) acetal to give the appropriately substituted {{α-[(haloalkylsulfonyl)methylene]benzyl-}amino}acetaldehyde di($C_1-C_4$ alkyl) acetal of formula VI. The formula VI intermediate is then reacted with excess trifluoroacetic acid to give the appropriately substituted 3-haloalkylsulfonyl-2-arylpyrrole of formula VII. The above reaction scheme is shown below in Flow Diagram I.

FLOW DIAGRAM I

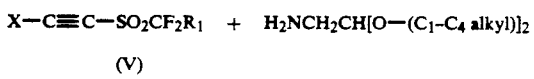

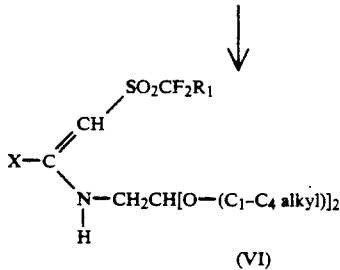

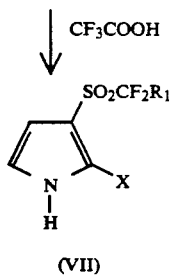

Certain haloalkylthio arylpyrroles of formula I may be prepared by reacting a 2-arylpyrrole compound with an excess of a halogalkylsulfenyl chloride compound and at least one molar equivalent of a base to give the appropriately substituted 5-haloalkyltiho-2-arylpyrrole compound of formula VIII. This reaction may be illustrated as follows:

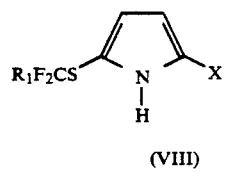

(VIII)

wherein X and $R_1$ are as described for formula I above.

Preparation of N-substituted formula I haloalkylthio, -sulfinyl and -sulfonyl arylpyrrole compounds can be achieved by reaction of the appropriately substituted formula I haloalkylthio-, sulfinyl or -sulfonyl arylpyrrole having R as hydrogen with an alkylating or acylating agent in the presence of an alkali metal alkoxide or hydride. For example, a formula I haloalkylthio, -sulfinyl or -sulfonyl arylpyrrole, wherein R is hydrogen and W, X, Y and Z are as described for formula I above, is reacted with an appropriate alkylating agent such as a $C_1-C_6$ alkylhalide in which the alkyl group is straight or branched and is optionally substituted with from one to three halogen atoms, one hydroxy, one cyano, one $C_1-C_4$ alkoxy, one $C_1-C_4$ alkylthio, one phenyl group, optionally substitued with from one to three halogen atoms, or one benzyloxy group, optionally substituted with from one to three halogen atoms, and an alkali metal alkoxide such as sodium or potassium t-butoxide. This reaction provides a haloalkylthio, -sulfinyl or -sulfonyl arylpyrrole having the same substituents as the starting material, but in addition is substituted on the nitrogen with a $C_1-C_6$ alkyl group optionally substituted as described above. This recation may be illustrated as follows:

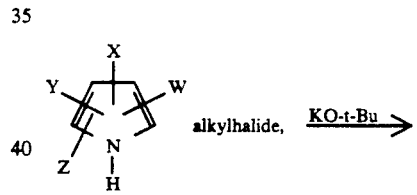

wherein W, X, Y and Z are as described for formula I above and R is $C_1-C_6$ alkyl optionally substituted as described above. In a similar reaction cyanogen bromide is substituted for the alkylhalide and yields the formula I haloalkylthio, -sulfinyl or -sulfonyl arylpyrrole having a carbonitrile, rather than an alkyl group, on the nitrogen.

Advantageously, the above-described alkylation procedure of the formula I haloalkylthio, -sulfinyl or -sulfonyl arylpyrrole comopunds, in which R is hydrogen may also be applied to the preparation of formula I haloalkylthio, -sulfinyl or -sulfonyl arylpyrroles having an $N-C_3-C_6$ alkenyl or $N-C_3-C_6$ alkynyl substituent. This N-substitution is obtained by simply substituting a $C_3-C_6$ alkenyl halide or $C_3-C_6$ alkynyl halide for the $C_1-C_6$ alkyl halide in the above-described reaction.

In a similar manner, preparation of N-acylated haloalkylthio, -sulfinyl or sulfonyl arylpyrrole compounds may be achieved by the reaction of an appropriately substituted formula I haloalkylthio, -sulfinyl or -sulfonyl arylpyrrole wherein R is hydrogen with an acylating agent in the presence of an alkali metal alkoxide. Acylating agents such as $C_1-C_6$ alkyl or $C_2-C_6$ alkenyl acid chloride, substituted $C_1-C_6$ alkyl or $C_2-C_6$ alkenyl acid chloride, benzoyl chloride, substituted benzoyl chloride, phenylchloroformate, substituted phenylchloroformate, $C_1-C_6$ alkyl or $C_2-C_6$ alkenylchloroformate, substituted $C_1-C_6$ alkyl or $C_2-C_6$ alkenylchloroformate, N-substituted carbamoyl chloride and the like may be employed. The reaction may be illustrated as follows:

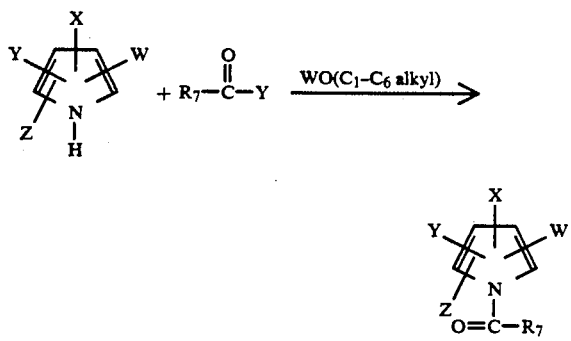

wherein Y is halogen, W is an alkali metal and W, X, Y, Z and $R_7$ are as described hereinabove for formula I.

N-substituted formula I haloalkylthio, -sulfinyl and -sulfonyl arylpyrrole compounds wherein R is $CH_2SQ$ may be prepared by reaction of the appropriately substituted formula I haloalkylthio, -sulfinyl or -sulfonyl arylpyrrole having R as chloromethyl with an alkali metal salt of an SQ compound in the presence of a base. For example, a formula I haloalkylthio, -sulfinyl or -sulfonyl arylpyrrole, wherein R is chloromethyl and W, X, Y and Z are as described for formula I above, is reacted with sodium dimethyldithiocarbamate dihydrate and a base such as sodium hydroxide. This reaction provides a haloalkylthio, -sulfinyl or -sulfonyl arylpyrrole having the same substituents as the starting material, but in addition is substituted on the nitrogen with a methyl dimethyldithiocarbamate group. This reaction may be illustrated as follows:

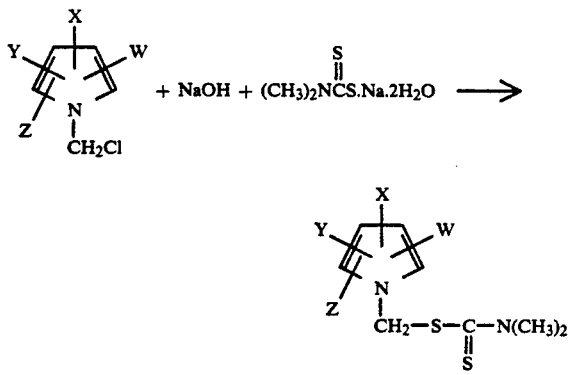

wherein W, X, Y and Z are as described for formula I above.

Pyrroles substituted on the nitrogen atom with $CH_2SQ$ are also described in copending U.S. patent application Ser. No. 07/803,295 filed concurrently herewith and incorporated herein by reference thereto.

Other methods for the preparation of formula I haloalkylthio, -sulfinyl and -sulfonyl arylpyrrole compounds will become apparent from the examples set forth below.

The compounds of the present invention are also effective for controlling or preventing the growth of phytopathogenic fungi in the presence of growing or harvested plants when applied to said plants at fungicidally effective rates. This will vary somewhat with the virulence of the pathogen in question and with other factors such as the environment in which treatment is conducted. These compounds are especially useful for the control of *Plasmopara viticola*, *Venturia inaequalis*, and *Eryiphe graminis F.sp. tritici* the causual agents of grape downy mildew, apple scab and wheat powdery mildew, respectively. Certain compounds of the invention may not only be employed to control fungi that have infected plants, but also may be applied to healthy plants or seeds or to the soil in which the plant is to be grown in order to prevent infestation.

To protect plants from phytopathogenic fungi, the compounds of formula I are applied to the foliage of the plant, to the seed of the plants, or to the soil in which the plant grows or is to be grown, in the form of a liquid, preferably in aqueous spray, or dust, or granular formulation. Solutions or suspensions containing from about 20 ppm to about 1,000 ppm, and preferably 50 ppm to 500 ppm, of formula I compounds are generally effective for this use.

It is understood that the compounds of the present invention can be applied singly or in combination with one or more other fungicidal compounds, such application being made either by combination of the fungicidal compounds or their formulations in a common container prior to use or by sequential application of the active fungicidal compounds or their formulations to the host crop or its environment. Compounds suitable for combination with the compounds of this invention are suggested by, but not limited to, the following: 4,6-dinitro-o-cresol, benalaxyl, benomyl, captafol, captan, carbendazim, chlorothalonil, copper, cymoxanil, cyproconazole, dichlobutrazole, dichlofluanid, diethofencarb, difenconazole, dimethomorph, diniconazole, dinocap, dithianon, fenarimol, fentin acetate, ferbam, flusilazole, folpet, fosetyl, hexaconazole, imazalil, iprodione, mancopper mancozeb, maneb, mepronil, mercuric oxide, metalaxyl, metiram, myclobutanil, nuarimol, ofurace, oxidixyl, penconazole, pencyuron, phosphorous acid, procymidone, propaconazole, propineb, pyrifenox, quintozene, sodium arsenite, sulphur, tebuconazole, thiabendazole, thiophanate methyl, thiram, tolclophos-methyl, triadimefon, triadimenol, triforine, vinclozolin, zineb, and ziram.

The compounds of the invention may be formulated as emulsifiable concentrates, flowable concentrates, or wettable powders which are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations include the compounds of the invention admixed with inert, solid or liquid diluents.

For example, wettable powders, dusts, and dust concentrate formulations can be prepared by grinding and blending together about 25% to about 85% by weight of formula I compounds and about 75% to about 15% by weight of a solid diluent such as bentonite, diatomaceous earth, kaolin, attapulgite, or the like, 1% to 5% by weight of a dispersing agent such as sodium lignosulfonate, and about 1% to 5% by weight of a nonionic surfactant, such as octylphenoxy polyethoxy ethanol, nonylphenoxy polyethoxy ethanol or the like.

A typical flowable liquid can be prepared by admixing about 30% to 90% by weight of a gelling agent such as bentonite, 2% to 5% by weight of a dispersing agent such as sodium ligosulfonate, about 1% by weight of polyethyleneglycol, and about 40% to 60% by weight of water.

A typical emulsifiable concentrate can be prepared by dissolving about 15% to 70% by weight of the active ingredient in about 85% to 30% by weight of a solvent such as isophorone, toluene, butyl cellosolve, methyl acetate, propylene glycol monomethyl ether, or the like and dispersing therein about 1% to 5% by weight of a nonionic surfactant such as an alkylphenoxy polyethoxy alcohol.

Some of the examples provided by way of illustration below utilize the schemes illustrated above and others provide a means for preparing other compounds of the invention which are not specifically described hereinabove. The invention is not to be deemed limited thereby except as defined in the claims.

EXAMPLE 1

Preparation of
{{α-{[(Trifluoromethyl)sulfonyl]methylene}benzyl-}amino}acetaldehyde diethyl acetal

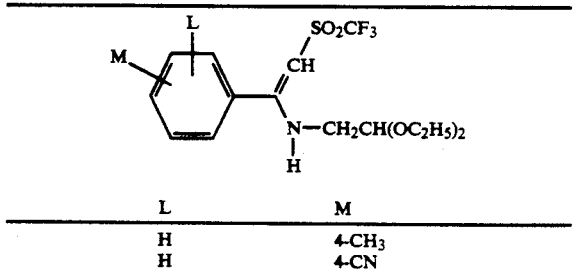

A solution of phenylethynyl trifluoromethylsulfone (2.43 g, 0.0104 mol) in ether is cooled to 5° C., treated with a solution of aminoacetaldehyde diethyl acetal (1.38 g, 0.0104 mol) in ether, stirred overnight at room temperature and concentrated in vacuo to obtain the title product as a red syrup (3.76 g) which is identified by NMR spectral analysis.

Following the above procedure, but substituting the appropriate substituted phenylethynyl trifluoromethylsulfone for phenylethynyl trifluoromethylsulfone yields the following compounds.

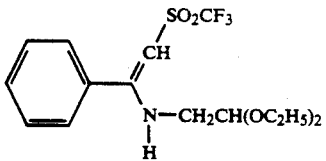

| L | M |
|---|---|
| H | 4-CH$_3$ |
| H | 4-CN |

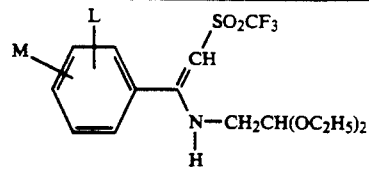

| L | M |
|---|---|
| H | 4-Br |
| H | 4-CF$_3$ |
| H | 4-C(CH$_3$)$_3$ |
| 3-Cl | 4-Cl |
| H | 4-F |
| H | 4-Cl |

EXAMPLE 2

Preparation of
2-Phenyl-3-[(trifluoromethyl)sulfonyl]pyrrole

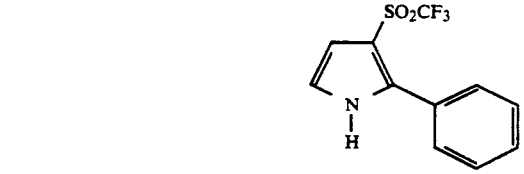

{{α-{[(Trifluoromethyl)sulfonyl]methylene}benzyl-)amino}acetaldehyde diethyl acetal (3.3 g, 0.009 mol) is treated with trifluoroacetic acid (15 mL), stirred overnight at room temperature, concentrated in vacuo, and chased with ethyl acetate to obtain a brown oil. Flash chromatography of the oil using silica gel and a 1:4 ethyl acetate/hexanes solution gives a brown solid. The solid is triturated in hexanes, filtered and air dried to give the title product as a tan solid (1.65 g, mp 116°–118° C.) which is identified by $^1$HNMR and $^{13}$CNMR spectral analyses.

Following the above procedure, but using the appropriately substituted {{α-{[(trifluoromethyl)sulfonyl]methylene}benzyl}amino}acetaldehyde diethyl acetal yields the following compounds.

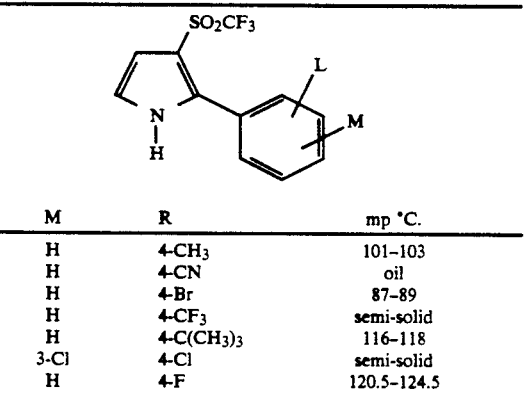

| M | R | mp °C. |
|---|---|---|
| H | 4-CH$_3$ | 101–103 |
| H | 4-CN | oil |
| H | 4-Br | 87–89 |
| H | 4-CF$_3$ | semi-solid |
| H | 4-C(CH$_3$)$_3$ | 116–118 |
| 3-Cl | 4-Cl | semi-solid |
| H | 4-F | 120.5–124.5 |

-continued

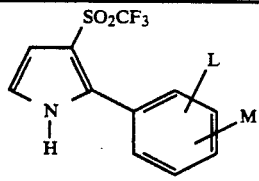

| M | R | mp °C. |
|---|---|---|
| H | 4-Cl | 87-90 |

EXAMPLE 3

Preparation of
{{p-Methoxy-α-{[(trifluoromethyl)sulfonyl]methylene}benzyl}amino}acetaldehyde diethyl acetal

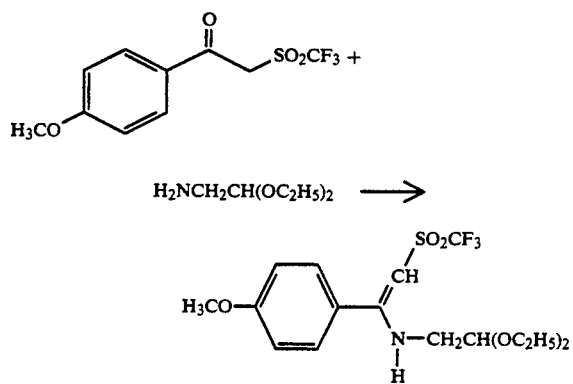

A solution of 4'-methoxy-2-[(trifluoromethyl)sulfonyl]acetophenone (6.0 g, 0.021 mol) in toluene is treated with aminoacetaldehyde diethyl acetal (2.8 g, 0.021 mol), heated at reflux overnight with removal of water, and concentrated in vacuo to obtain the title product as an oil. This oil is used in Example 4 without further purification.

EXAMPLE 4

Preparation of
2-(p-Methoxyphenyl)-3-[(trifluoromethyl)sulfonyl]pyrrole

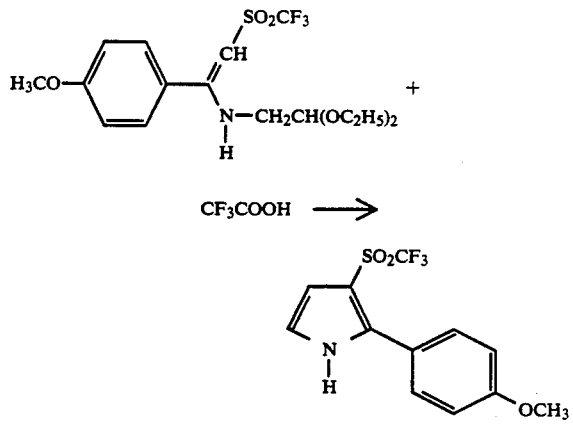

The oil obtained in Example 3 is treated with trifluoroacetic acid (20 mL), stirred for several hours at room temperature, concentrated in vacuo and chased with ethyl acetate to obtain an oil. Flash chromatography of the oil using silica gel and a 1:4 ethyl acetate/heptane solution gives a yellow semi-solid. Recrystallization of the semi-solid gives the title product as a yellow solid (0.88 g, mp 138.5°-140.5° C.) which is identified by $^1$HNMR and $^{13}$CNMR spectral analyses.

EXAMPLE 5

Preparation of
5-Bromo-2-(p-chlorophenyl)-3-[(trifluoromethyl)sulfonyl]pyrrole

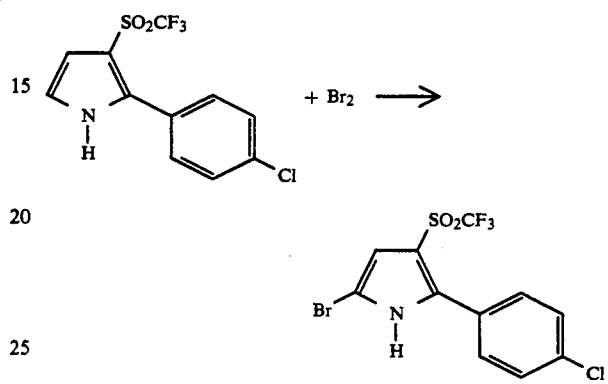

A solution of 2-(p-chlorophenyl)-3-[(trifluoromethyl)sulfonyl]pyrrole (1.0 g, 0.00323 mol) in chloroform is cooled, treated with a solution of bromine (0.52 g, 0.00323 mol) in chloroform, stirred at room temperature overnight, diluted with chloroform, washed with water and brine, dried over anhydrous magnesium sulfate and concentrated in vacuo to obtain a dark syrup. Flash chromatography of the syrup using silical gel and a 1:5 ethyl acetate/hexanes solution gives the title product as an off-white solid (0.31 g, mp 73°-76° C.) which is identified by $^1$HNMR spectral analysis.

EXAMPLE 6

Preparation of
5-Chloro-2-(p-chlorophenyl)-3-[(trifluoromethyl)sulfonyl]pyrrole

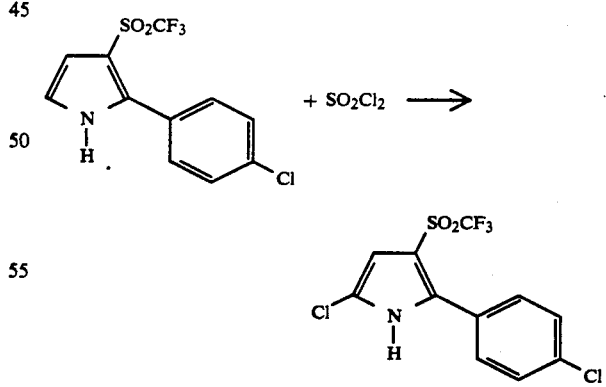

A solution of 2-(p-chlorophenyl)-3-[(trifluoromethyl)sulfonyl]pyrrole (1.0 g, 0.00323 mol) in acetic acid is treated with thionyl chloride (0.43 g, 0.00323 mol), stirred for 30 minutes, poured into water and decanted to obtain a residue. The residue is dissolved in ethyl acetate and the organic solution is washed with brine, dried over anhydrous magnesium sulfate and concentrated in vacuo to obtain a dark syrup. Flash chromatography of the syrup using silica gel and a 1:5 ethyl acetate/hexanes solution gives the title product as a yellow solid (0.43 g, mp 109°–112° C.) which is identified by $^1$HNMR spectral analysis.

Following the procedures of Examples 5 and 6, but substituting the appropriately substituted 2-phenyl-3-[(trifluoromethyl)sulfonyl]pyrrole for 2-(p-chlorophenyl)-3-[(trifluoromethyl)sulfonyl]pyrrole and using one or two equivalents of halogenating reagent yields the following compounds.

| X  | Y  | L    | M        | mp °C.      |
|----|----|------|----------|-------------|
| Br | Br | H    | 4-Cl     | 149–150     |
| Cl | Cl | H    | 4-Cl     | 140–143     |
| Br | Br | H    | 4-F      | 167–169     |
| Br | Br | 3-Cl | 4-Cl     | 148–149     |
| Br | Br | H    | 4-CH$_3$ | 183.5–185   |
| Cl | Cl | 3-Cl | 4-Cl     | 147–149     |
| Br | Br | H    | 4-CN     | 214–217     |
| H  | Br | H    | 4-CN     | syrup       |
| Cl | Cl | H    | 4-CH$_3$ | 170–171     |
| Br | Br | H    | H        | 158 (dec)   |
| Br | Br | H    | 4-Br     | 146–148     |
| Br | Br | H    | 4-CF$_3$ | 208–211     |
| Cl | Cl | H    | 4-Br     | 126–129     |
| Br | Br | H    | 4-C(CH$_3$)$_3$ | 195.5–196.5 |
| Br | Br | H    | 4-OCH$_3$ | 138.5–150  |

EXAMPLE 7

Preparation of
5-(p-Chlorophenyl)-4-[(trifluoromethyl)sulfonyl]pyrrole-2-carbonitrile

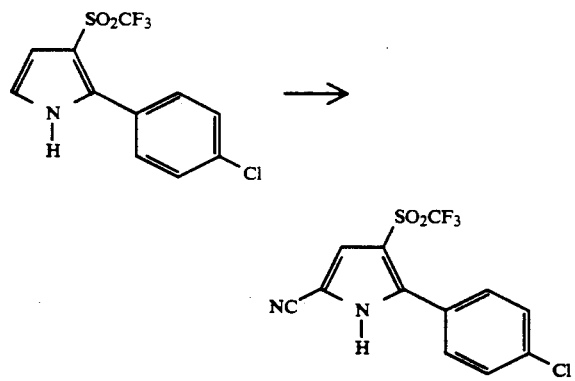

A solution of 2-(p-chlorophenyl)-3-[(trifluoromethyl)sulfonyl]pyrrole (0.9 g, 0.00291 mol) in acetonitrile is cooled, treated with chlorosulfonyl isocyanate (0.66 g, 0.00465 mol) under nitrogen, stirred overnight at room temperature, cooled, treated with dimethylformamide (1.06 g, 0.0145 mol), stirred at room temperature for five hours, poured into water and extracted with ether. The combined organic extracts are washed with brine, dried over anhydrous magnesium sulfate and concentrated in vacuo to obtain a dark syrup. Flash chromatography of the syrup using silica gel and a 1:3 ethyl acetate/hexanes solution gives a pale yellow syrup which is placed onto a silica gel plate and eluted with a 1:3 ethyl acetate/hexanes solution to give the title product as a waxy solid (mp 112°–122° C.) which is identified by $^1$HNMR spectral analysis.

EXAMPLE 8

Preparation of
3-Bromo-5-(p-chlorophenyl)-4-[(trifluoromethyl)sulfonyl]pyrrole-2-carbonitrile

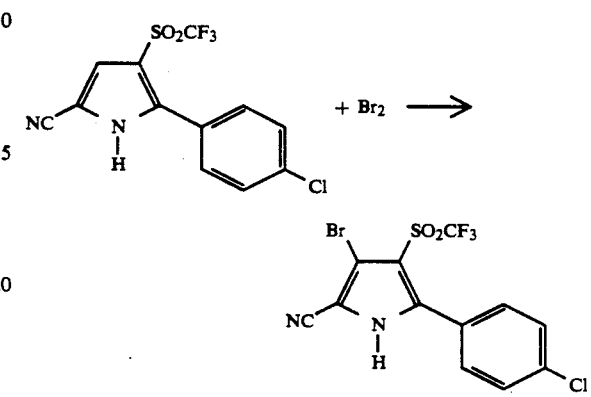

A solution of 5-(p-chlorophenyl)-4-[(trifluoromethyl)sulfonyl]pyrrole-2-carbonitrile (0.87 g, 0.0026 mol) in dioxane is cooled, treated with bromine (0.46 g, 0.00286 mol), stirred at room temperature for two hours, treated with additional bromine (0.21 g, 0.0013 mol), stirred overnight at room temperature, poured into water and extracted with ethyl acetate. The combined organic extracts are washed with water, saturated sodium meta-bisulfite solution and brine, dried over anhydrous magnesium sulfate and concentrated in vacuo to obtain a yellow syrup. Flash chromatography of the syrup using silica gel and a 1:4 ethyl acetate/hexanes solution gives the title product as a tan solid (0.27 g, mp 170°–185° C.) which is identified by $^1$HNMR spectral analysis.

EXAMPLE 9

Preparation of
2,3-Dibromo-5-(p-chlorophenyl)-1-(ethoxymethyl)-4-[(trifluoromethyl)sulfonyl]pyrrole

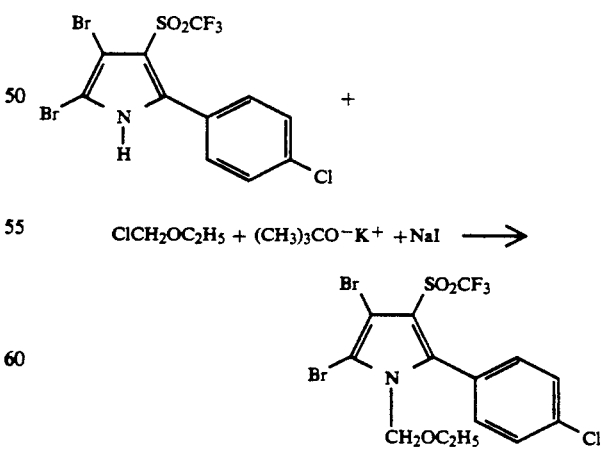

A solution of potassium tert-butoxide (0.62 g, 0.0055 mol) in tetrahydrofuran is treated with 2,3-dibromo-5-(p-chlorophenyl)-4-[(trifluoromethyl)sulfonyl]pyrrole (2.34 g, 0.005 mol), stirred for 15 minutes, treated with sodium iodide (0.82 g, 0.0055 mol), stirred for five minutes, treated with a solution of chloromethyl ethyl ether (0.52 g, 0.0055 mol) in tetrahydrofuran, stirred at room temperature for several hours, poured into water and extracted with ether. The combined organic extracts are washed with water and brine, dried over anhydrous sodium sulfate and concentrated in vacuo to give an orange oil. The oil is slurried in hexane and filtered to obtain the title product as a pale yellow solid (1.95 g, mp 133°–135° C.) which is identified by $^1$HNMR and $^{19}$FNMR spectral analyses.

Following the above procedure, but substituting bromoacetonitrile for chloromethyl ethyl ether yields 2,3-dibromo-5-(p-chlorophenyl-4-[(trifluoromethyl)sulfonyl]pyrrole-1-acetonitrile, mp 191.5°–193.5° C.

EXAMPLE 10

Preparation of N-(hydroxymethyl)acetamide

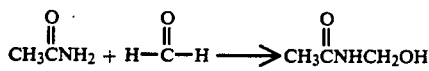

Acetamide (200 g, 3.4 mol) is added to a solution of potassium carbonate (20 g, 0.144 mol) in an aqueous formaldehyde solution (274 g, 37%, 3.4 mol). The reaction mixture is heated to 75° C., stirred for 3½ hours at room temperature, quenched with dry ice, diluted with acetone, dried with anhydrous sodium sulfate and filtered. The filtrate is dried with anhydrous sodium sulfate, filtered and concentrated in vacuo to give the title product as an oil (309 g) which is identified by $^1$HNMR spectral analysis.

EXAMPLE 11

Preparation of N-(hydroxymethyl)acetamide acetate (ester)

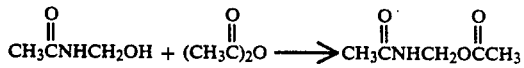

Acetic anhydride (25 g) and pyridine (10 drops) is added to N-(hydroxymethyl)acetamide (9 g, 0.1 mol). The reaction mixture is stirred overnight at room temperature, concentrated in vacuo and chased with xylene to give the title product as an oil (11.9 g, 0.9 mol) which is identified by $^1$HNMR spectral analysis.

EXAMPLE 12

Preparation of N-{{2,3-Dibromo-5-(p-chlorophenyl)-4-(trifluoromethyl)sulfonyl]pyrrol-1-yl)methyl)acetamide

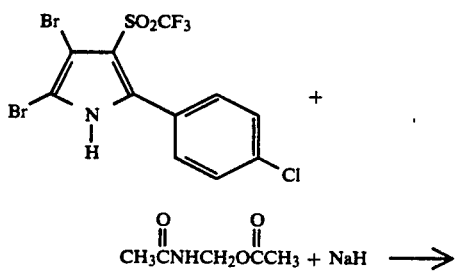

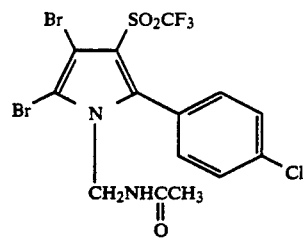

A mixture of sodium hydride (0.5 g, 60%, 0.0125 mol) and tetrahydrofuran is treated with 2,3-dibromo-5-(p-chlorophenyl)-4-[(trifluoromethyl)sulfonyl]pyrrole (4.67 g, 0.01 mol), stirred for 15 minutes and treated with a solution of N-(hydroxymethyl)acetamide acetate (ester) (1.64 g, 0.0125 mol) in tetrahydrofuran. The reaction mixture is heated at reflux for 18 hours, concentrated in vacuo and poured into a water/ether mixture. The organic phase is separated, washed with water and brine, dried over anhydrous sodium sulfate and concentrated in vacuo to obtain the title product as a white solid (4.56 g).

EXAMPLE 13

Preparation of 2,3-Dibromo-1-(chloromethyl)-5-(p-chlorophenyl)-4-[(trifluoromethyl)sulfonyl]pyrrole

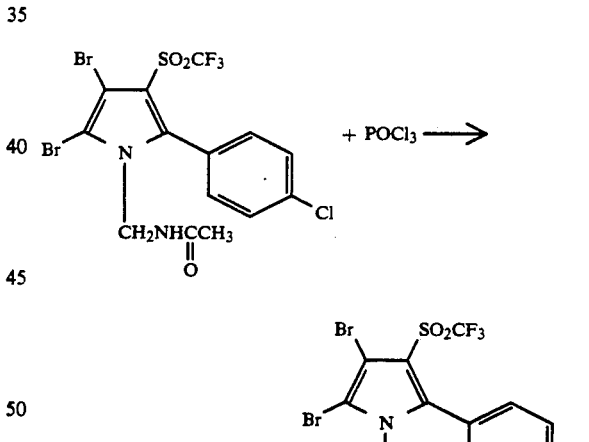

N-{{2,3-Dibromo-5-(p-chlorophenyl)-4-[(trifluoromethyl)sulfonyl]pyrrol-1-yl}methyl}acetamide (4.5 g, 0.00835 mol) is added to phosphoros oxychloride (15 mL). The reaction mixture is refluxed for 3½ hours, poured into water, stirred overnight and filtered to obtain a solid. The solid is dissolved into methylene chloride and the solution is dried over anhydrous sodium sulfate and concentrated in vacuo to obtain the title product as a yellow solid (3.8 g, mp 153°–156° C.) which is identified by $^1$HNMR and $^{13}$CNMR spectral analyses.

EXAMPLE 14

Preparation of
{2,3-Dibromo-5-(p-chlorophenyl)-4-[(trifluoromethyl)-sulfonyl]pyrrol-1-yl}methyl dimethyldithiocarbamate

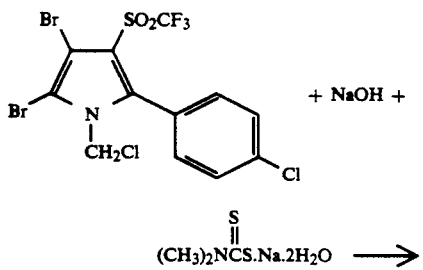

2,3-Dibromo-1-(chloromethyl)-5-(p-chlorophenyl)-4-[(trifluoromethyl)sulfonyl]pyrrole (1.0 g, 0.00194 mol) is added to a mixture of sodium hydroxide (0.084 g, 0.0021 mol), sodium dimethyldithiocarbamate dihydrate (0.376 g, 0.0021 mol) and dimethylformamide. The reaction mixture is stirred for six hours at room temperature, poured into water and extracted with ethyl acetate. The combined organic extracts are washed with water and brine, dried over anhydrous sodium sulfate and concentrated in vacuo to obtain a yellow gum. The gum is stirred with hexanes overnight and filtered to give the title product as a white solid (0.37 g, mp 185°-187° C.) which is identified by $^1$HNMR and $^{19}$FNMR spectral analyses.

Following the above procedure, but using p-chlorohippuric acid and p-toluic acid for sodium dimethyldithiocarbamate dihydrate yields {2,3-dibromo-5-(p-chlorophenyl)-4-[(trifluoromethyl)sulfonyl]pyrrole-1-yl}methyl p-chlorohippurate, mp 74°-78° C. and {2,3-dibromo-5-(p-chlorophenyl)-4-[(trifluoromethyl)-sulfonyl]pyrrol-1-yl}methyl p-toluate, mp 148°-151° C., respectively.

EXAMPLE 15

Preparation of
2-(p-Chlorophenyl)-5-[(trifluoromethyl)thio]pyrrole

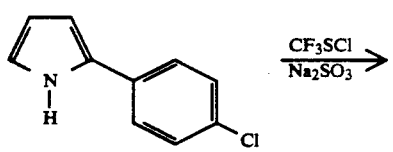

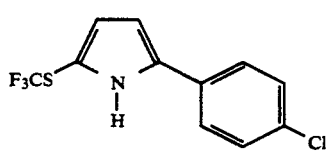

Trifluoromethylsulfenyl chloride is bubbled into a solution of 2-(p-chlorophenyl)pyrrole (0.5 g, 0.00281 mol) and sodium carbonate (0.36 g, 0.00338 mol) in ether at −30° C. under nitrogen. The reaction mixture is stirred for ½ hour and diluted with a water/ether mixture. The organic phase is separated, washed with brine, dried over anhydrous magnesium sulfate and concentrated in vacuo to give the title product as a purple solid (0.78 g, mp 34°-39° C.) which is identified by $^1$HNMR and $^{13}$CNMR spectral analyses.

Following the above procedure, but substituting difluoromethylsulfenyl chloride for trifluoromethylsulfenyl chloride yields 2-(p-chlorophenyl)-5-[(difluoromethyl)thio]pyrrole, mp 42°-46° C.

EXAMPLE 16

Preparation of
3-Bromo-2-(p-chlorophenyl)-5-[(trifluoromethyl)thio]-pyrrole

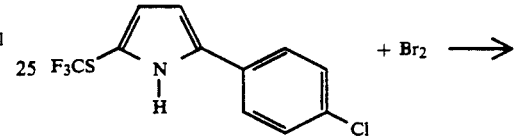

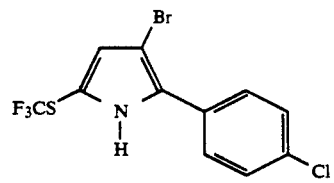

A solution of 2-(p-chlorophenyl)-5-[(trifluoromethyl)thio]pyrrole (1.94 g, 0.00699 mol) in chloroform is cooled, treated with a solution of bromine (1.16 g, 0.00699 mol) in chloroform, stirred for two hours, washed with water and brine, dried over anhydrous magnesium sulfate and concentrated in vacuo to obtain a dark syrup. Flash chromatography of the syrup using silica gel and a 1:10 ethyl acetate/hexanes solution gives the title product as a pink syrup (2.0 g) which is identified by $^1$HNMR and $^{13}$CNMR spectral analyses.

Following the above procedure, but using the appropriately substituted 2-(p-chlorophenyl-5-(substituted methyl)thio]pyrrole and two equivalents of bromine yields 3,4-dibromo-2-(p-chlorophenyl)-5-[(trifluoromethyl)thio]pyrrole, mp 105°-107° C. and 3,4-dibromo-2-(p-chlorophenyl)-5-[(difluoromethyl)thio]pyrrole, mp 82°-92° C.

EXAMPLE 17

Preparation of
3-Bromo-2-(p-chlorophenyl)-5-[(trifluoromethyl)sulfinyl]pyrrole

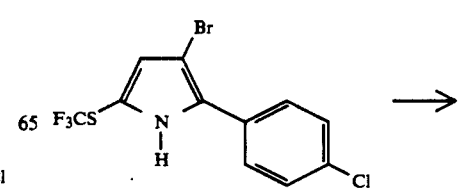

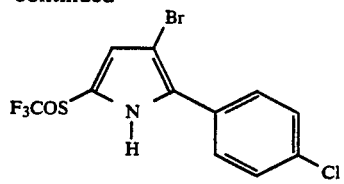

A solution of 3-bromo-2-(p-chlorophenyl)-5-[(trifluoromethyl)thio]pyrrole (0.65 g, 0.00182 mol) in chloroform is cooled with an ice-water bath, treated with a solution of 3-chloroperoxybenzoic acid (0.52 g, 60% pure, 0.00182 mol) in chloroform, stirred for two hours, treated with saturated sodium metabisulfite solution, diluted with methylene chloride, washed with saturated sodium hydrogen carbonate solution and brine, dried over anhydrous magnesium sulfate and concentrated in vacuo to obtain a white solid. Flash chromatography of the solid using silica gel and a 1:10 ethyl acetate/hexanes solution gives the title product as a white solid (0.34 g, mp 177°–179° C.) which is identified by $^1$HNMR spectral analysis.

Following the above procedure, but using 3,4-dibromo-2-(p-chlorophenyl)-5-[(trifluoromethyl)thio]pyrrole for 3-bromo-2-(p-chlorophenyl)-5-[(trifluoromethyl)thio]pyrrole yields 3,4-dibromo-2-(p-chlorophenyl)-5-[(trifluoromethyl)sulfinyl]pyrrole, mp 173°–176° C.

EXAMPLE 18

Preparation of
3-Bromo-2-(p-chlorophenyl)-5-[(trifluoromethyl)sulfonyl]pyrrole

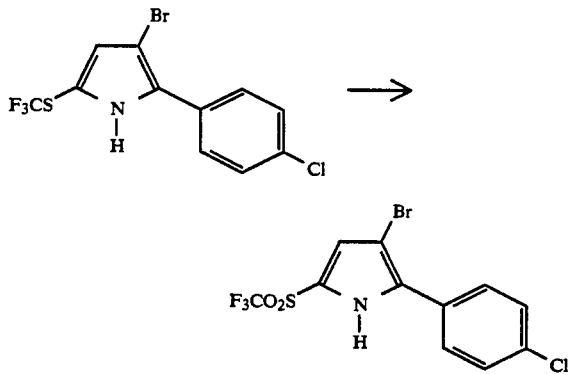

A solution of 3-bromo-2-(p-chlorophenyl)-5-[(trifluoromethyl)thio]pyrrole (0.70 g, 0.00196 mol) in chloroform is cooled with an ice-water bath, treated with a solution of 3-chloroperoxybenzoic acid (1.3 g, 60% pure, 0.0045 mol) in chloroform, stirred for two hours, warmed to room temperature, stirred overnight, treated with saturated sodium metabisulfite solution, diluted with methylene chloride, washed with saturated sodium hydrogen carbonate solution and brine, dried over anhydrous magnesium sulfate and concentrated in vacuo to obtain a white solid. Flash chromatography of the solid using silica gel and a 1:10 ethyl acetate/hexanes solution gives the title product as a white solid (0.48 g, mp 155°–159° C.) which is identified by $^1$HNMR and $^{19}$FNMR spectral analyses.

Following the above procedure, but substituting 3,4-dibromo-2-(p-chlorophenyl)-5-[(difluoromethyl)thio]pyrrole for 3-bromo-2-(p-chlorophenyl)-5-[(trifluoromethyl)sulfonyl]pyrrole yields 3,4-dibromo-2-(p-chlorophenyl)-5-[(difluoromethyl)sulfonyl]pyrrole, mp 194°–196° C. (dec).

EXAMPLE 19

Preparation of
3,4-Dibromo-2-(p-chlorphenyl)-5-[trifluoromethyl)sulfonyl]pyrrole

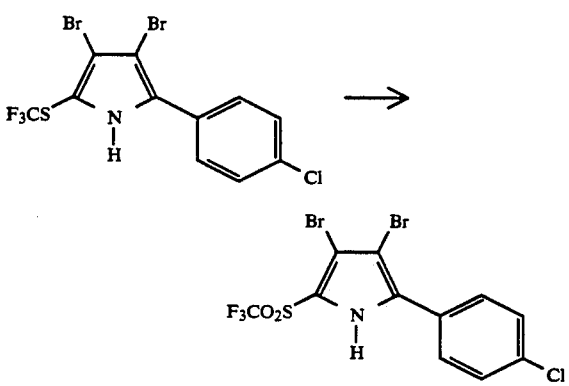

A solution of 3,4-dibromo-2-(p-chlorophenyl)-5-[(trifluoromethyl)thio]pyrrole (0.9 g, 0.00207 mol) in tetrahydrofuran is cooled with an ice-water bath, treated with a solution of monoperoxyphthalic acid, magnesium salt hexahydrate (1.4 g, 80% pure, 0.00227 mol) in tetrahydrofuran, stirred overnight at room temperature, treated with saturated sodium metabisulfite solution, diluted with ethyl acetate, washed with saturated sodium hydrogen carbonate solution and brine, dried over anhydrous magnesium sulfate and concentrated in vacuo to obtain a yellow residue. Flash chromatography of the residue using silica gal and a 1:10 ethyl acetate/hexanes solution gives the title product as a white solid (0.21 g, mp 165°–168° C.) which is identified by $^1$HNMR and $^{19}$FNMR spectral analyses.

EXAMPLE 20

Preparation of
3-(p-Chlorophenyl)-4-[(trifluoromethyl)sulfonyl]pyrrole

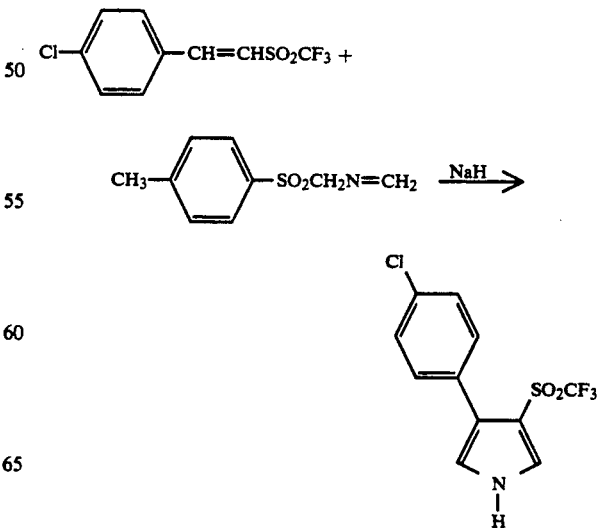

A mixture of sodium hydride (0.31 g, 60%, 0.0077 mol) and ether is treated dropwise with a solution of p-chlorostyryl trifluoromethylsulfone (1.73 g, 0.0064 mol), N-methylene-1-(p-tolylsulfonyl)methylamine (1.25 g, 0.0064 mol), ether (20 mL) and dimethylsulfoxide (10 mL) with stirring under nitrogen. The reaction mixture is stirred for one hour, diluted with water and extracted with ether. The combined organic extracts are washed with brine, dried over anhydrous magnesium sulfate and concentrated in vacuo to obtain a yellow syrup. Flash chromatography of the syrup using silica gel and a 1:2 ethyl acetate/hexanes solution gives the title product as a white solid (1.4 g, mp 138°–141° C.) which is identified by ¹HNMR, ¹⁹FNMR and ¹³CNMR spectral analyses.

EXAMPLE 21

Preparation of 2-Bromo-3-(p-chlorophenyl)-4-[(trifluoromethyl)sulfonyl]pyrrole

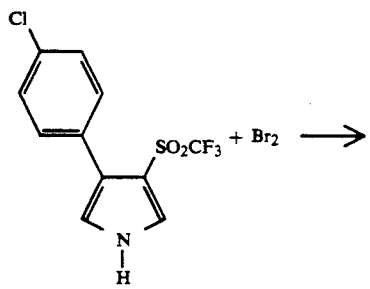

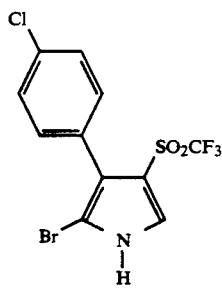

A solution of 2-bromo-3-(p-chlorophenyl)-4-[(trifluoromethyl)sulfonyl]pyrrole (0.5 g, 0.00161 mol) in chloroform is cooled with an ice-water bath, treated with a solution of bromine (0.258 g, 0.00161 mol) in chloroform, stirred for several hours, diluted with methylene chloride, washed with water and brine, dried over anhydrous magnesium sulfate and concentrated in vacuo to obtain a white solid. Flash chromatography of the solid using silica gel and a 1:3 ethyl acetate/hexanes solution gives the title product as a white solid (0.54 g, mp 163°–165° C.) which is identified by ¹HNMR and ¹³CNMR spectral analyses.

Following the above procedure, but using two equivalents of bromine yields 2,5-dibromo-3-(p-chlorophenyl)-4-[(trifluoromethyl)sulfonyl]pyrrole, mp 224°–226° C.

EXAMPLE 22

Preparation of 2-(p-Chlorophenyl)-3-nitro-5-[(trifluoromethyl)thio]-pyrrole and 5-(p-Chlorophenyl)-3-nitro-2-[(trifluoromethyl)thio]-pyrrole

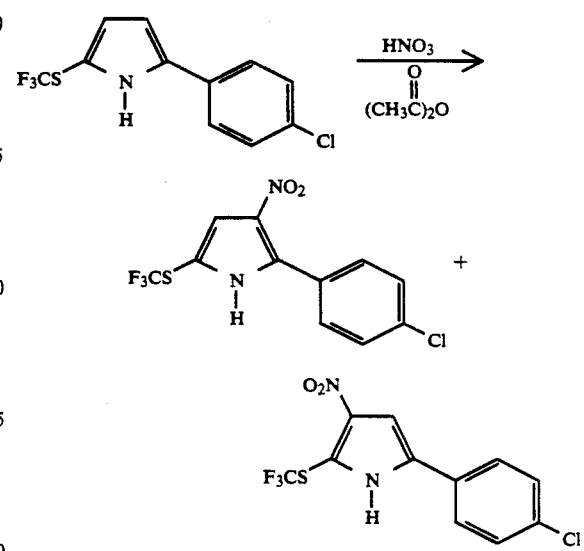

A solution of 2-(p-chlorophenyl)-5-[(trifluoromethyl)thio]pyrrole (1.0 g, 0.0036 mol) in acetic acid is cooled with an ice bath, treated with nitric acid (0.24 g, 0.00378 mol), stirred for two hours, poured into ice-water and stirred for one hour. The aqueous solution is filtered and the filter cake is washed with water and dried in a vacuum dessicator to obtain a tan solid. Flash chromatography of the solid using silica gel and a 1:10 ethyl acetate/hexanes solution gives 2-(p-chlorophenyl)-3-nitro-5-[(trifluoromethyl)thio]pyrrole as a yellow solid (0.45 g, mp 143°–145° C.) and 5-(p-chlorophenyl)-3-nitro-2-[(trifluoromethyl)thio]pyrrole as a yellow solid (0.17 g, mp 185°–193° C.) Both products are identified by ¹HNMR, ¹⁹FNMR and ¹³CNMR spectral analyses.

EXAMPLE 23

Preparation of 3-Bromo-5-(p-chlorophenyl)-4-nitro-2[(trifluoromethyl)thio]pyrrole

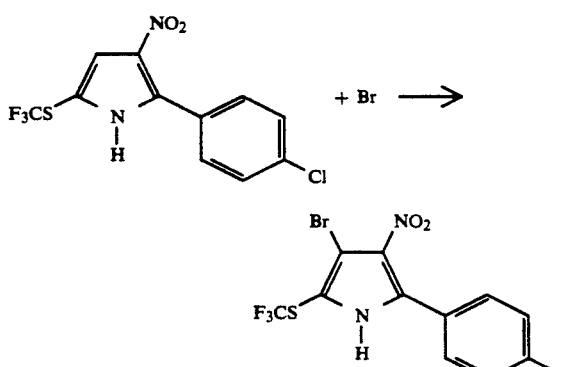

A solution of 2-(p-chlorophenyl)-3-nitro-5-[(trifluoromethyl)thio]pyrrole (0.35 g, 0.0011 mol) and sodium acetate (0.11 g, 0.0013 mol) in acetic acid is treated with a solution of bromine (0.21 g, 0.0013 mol) in acetic acid, stirred for one hour, poured into water and extracted with ethyl acetate. The combined organic extracts are washed with water and brine, dried over anhydrous magnesium sulfate and concentrated in vacuo to obtain a residue. Flash chromatography of the residue using silica gel and a 1:9 ethyl acetate/hexanes solution gives the title product as a yellow solid (0.25 g, mp 160°–165° C.) which is identified by $^1$HNMR, $^{19}$FNMR and $^{13}$CNMR spectral analyses.

EXAMPLE 24

Preparation of 2-(p-Chlorophenyl)-3-nitro-5-[(trifluoromethyl)sulfonyl]pyrrole

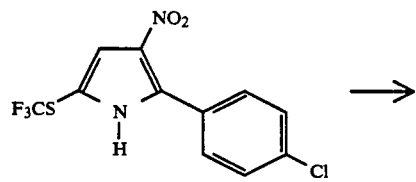

A solution of 2-(p-chlorophenyl)-3-nitro-5-[(trifluoromethyl)thio]pyrrole (0.24 g, 0.000744 mol) in chloroform is cooled with an ice bath, treated with 3-chloroperoxybenzoic acid (0.49 g, 60%, 0.00171 mol) and stirred for one hour. The cooling bath is removed and the reaction mixture is stirred for one hour, treated with saturated sodium bisulfite solution, diluted with methylene chloride, washed with saturated sodium hydrogen carbonate solution and brine, dried over anhydrous magnesium sulfate and concentrated in vacuo to obtain a yellow syrup. Flash chromatography of the syrup using silica gel and 1:3 ethyl acetate/hexanes solution gives the title product as a yellow solid (0.26 g, mp 97°–99° C.) which is identified by $^1$HNMR and 19FNMR spectral analyses.

EXAMPLE 25

Preparation of 2-(p-Chlorophenyl)-5-nitro-3-[(trifluoromethyl)sulfonyl]pyrrole

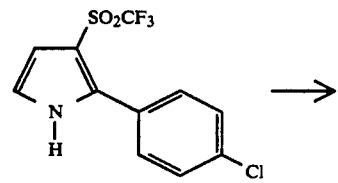

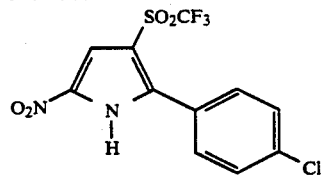

A solution of 2-(p-chlorophenyl)-3-[(trifluoromethyl)sulfonyl]pyrrole (1.0 g, 0.00323 mol) in acetic anhydride is cooled with an ice bath, treated with nitric acid (0.15 mL, 0.00329 mol), warmed to room temperature, stirred for 20 hours and poured into water. The mixture is decanted and the insolubles are dissolved in ethyl acetate. The ethyl acetate solution is washed with brine, dried over anhydrous magnesium sulfate and concentrated in vacuo to obtain an amber residue. Flash chromatography of the residue using silica gel and a 1:1 ethyl acetate/hexanes solution gives the title product as a tan solid (0.43 g, mp 174°–180° C.) which is identified by $^1$HNMR spectral analysis.

EXAMPLE 26

Preparation of 5-(p-Chlorophenyl)pyrrol-5-yl trichloromethyl ketone

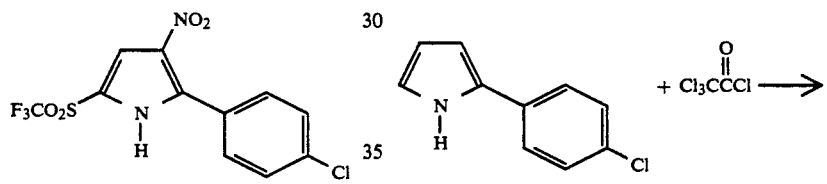

A solution of trichloroacetyl chloride (11.26 g, 0.0619 mol) in ether is treated with a solution of 2-(p-chlorophenyl)pyrrole (10.0 g, 0.0503 mol) in ether, stirred for four hours at room temperature, treated with saturated potassium carbonate solution and diluted with ethyl acetate. The organic phase is separated, washed with brine, dried over anhydrous magnesium sulfate and concentrated in vacuo to obtain a yellow solid. The solid is recrystallized from 2-propanol to give the title product as a yellow solid (12.63 g, mp 166°–168° C.) which is identified by $^1$HNMR spectral analysis.

EXAMPLE 27

Preparation of Methyl 5-(p-chlorophenyl)pyrrole-2-carboxylate

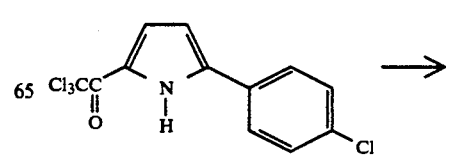

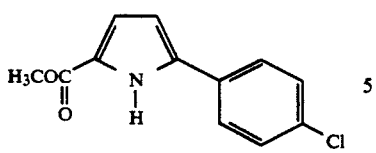

A solution of sodium methoxide (12.73 mL of 4.38 M solution in methanol, 0.0556 mol) in methanol is cooled with an ice bath, treated with 5-(p-chlorophenyl)pyrrol-5-yl trichloromethyl ketone (6.0 g, 0.0186 mol), stirred for two hours, diluted with water and filtered to obtain a solid. The solid is washed with water and dried overnight in a vacuum dessicator to give the title product as a tan solid (4.23 g, mp 177°–179° C.) which is identified by ¹HNMR spectral analysis.

Following the above procedure, but substituting sodium ethoxide and ethanol for sodium methoxide and methanol yields ethyl 5-(p-chlorophenyl)pyrrole-2-carboxylate, mp 148°–150 5° C.

EXAMPLE 28

Preparation of Methyl 5-(p-chlorophenyl)-4-[(trifluoromethyl)thio]pyrrole-2-carboxylate

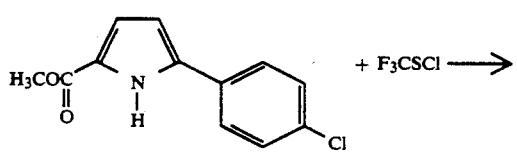

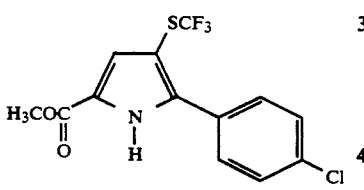

Trifluoromethanesulfonic acid (0.27 g, 0.001795 mol) is added to a solution of methyl 5-(p-chlorophenyl)pyrrole-2-carboxylate (4.23 g, 0.01795 mol) in methylene chloride (70 mL) at −30° C. This mixture is treated with trifluoromethylsulfenyl chloride (4.0 g, 0.0293 mol), stirred for 30 minutes at −15° C., warmed to room temperature with stirring for three hours, diluted with methylene chloride, washed with saturated sodium hydrogen carbonate solution and brine, dried over anhydrous magnesium sulfate and concentrated in vacuo to obtain the title product as an off-white solid (5.44 g, mp 133°–137° C.) which is identified by ¹HNMR spectral analysis.

EXAMPLE 29

Preparation of 5-(p-Chlorophenyl)-4-(trifluoromethyl)thio]pyrrole-2-carboxylic acid

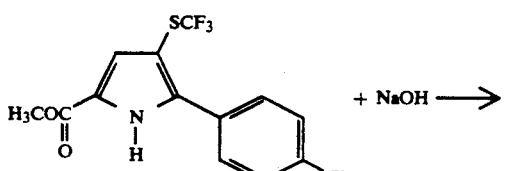

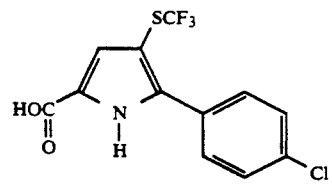

A mixture of methyl 5-(p-chlorophenyl)-4-[(trifluoromethyl)thio]pyrrole-2-carboxylate (4.89 g, 0.0146 mol) and sodium hydroxide (1.75 g, 0.0437 mol) in a 2:1 methanol/water solution (150 mL) is warmed to 60° C., stirred for three hours, cooled to room temperature with stirring overnight and concentrated in vacuo to remove most of the methanol. The resulting aqueous solution is treated with 10% hydrochloric acid and a white precipitate forms. Ethyl acetate is added and the organic phase is separated, washed with brine, dried over anhydrous magnesium sulfate and concentrated in vacuo to give the title product as an off-white solid (4.98 g, mp 176°–178° C.) which is identified by ¹HNMR spectral analysis.

EXAMPLE 30

Preparation of 2-(p-Chlorophenyl)-3-[(trifluoromethyl)thio]pyrrole

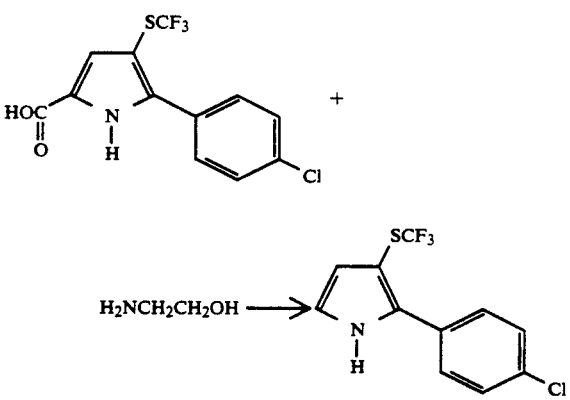

A mixture of 5-(p-chlorophenyl)-4-[trifluoromethyl)thio]fluoromethyl)thio]pyrrole-2-carboxylic acid (0.5 g, 0.00155 mol) in ethanolamine (1.5 mL) is stirred at 160° C. for five hours, cooled to room temperature overnight with stirring, poured into water and extracted with ether. The combined organic extracts are washed with brine, dried over anhydrous magnesium sulfate and concentrated in vacuo to obtain a yellow syrup. Flash chromatography of the syrup using silica gel and a 1:4 ethyl acetate/hexanes solution gives the title product as an off-white solid (0.11 g, mp 59°–64° C.) which is identified by ¹HNMR and ¹⁹FNMR spectral analyses.

EXAMPLE 31

Preparation of 2,3-Dibromo-5-(p-chlorophenyl)-4-[(trifluoromethyl)thio]pyrrole

A solution of 5-(p-chlorophenyl)-4-[(trifluoromethyl)thio]pyrrole-2-carboxylic acid (0.75 g, 0.00233 mol) and sodium acetate (0.84 g, 0.0103 mol) in acetic acid (15 mL) is treated dropwise with a solution of bromine (0.82 g, 0.00513 mol) in acetic acid (7.5 mL), stirred for two hours, diluted with water and extracted with ether. The combined organic extracts are washed with water, saturated metabisulfite solution, saturated sodium hydrogen carbonate solution and brine, dried over anhydrous magnesium sulfate and concentrated in vacuo to obtain a yellow syrup. Flash chromatography of the syrup using silica gel and a 1:10 ethyl acetate/hexanes solution gives the title product as a tan solid (0.52 g, mp 107°–113° C.) which is identified by $^1$HNMR, $^{13}$CNMR and $^{19}$FNMR spectral analyses.

EXAMPLE 32

Preparation of Ethyl 4-(p-chlorophenyl)-5-[(trifluoromethyl)thio]pyrrole-3-carboxylate

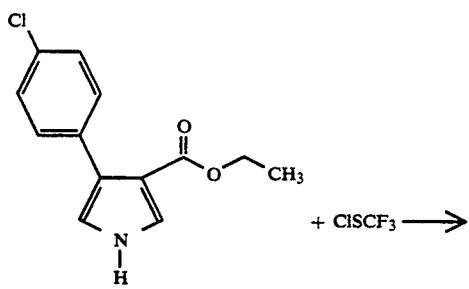

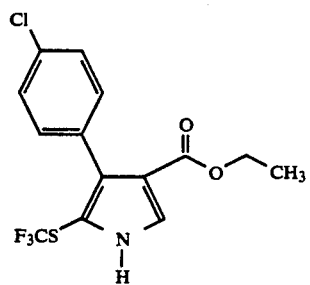

A solution of ethyl 4-(p-chlorophenyl)pyrrole-3-carboxylate (9.0 g, 0.036 mol) in methylene chloride (180 mL) is treated with trifluoromethylsulfenyl chloride (4.9 g, 0.036 mol) with stirring for 45 minutes at −30° C. The reaction mixture is warmed to room temperature and stirred for several hours. Since a TLC shows some starting material present, the reaction mixture is cooled to −30° C., treated with additional trifluoromethylsulfenyl chloride (1.3 g, 0.0095 mol), warmed to room temperature overnight with stirring, washed with water, saturated sodium hydrogen carbonate solution and brine, dried over anhydrous magnesium sulfate and concentrated in vacuo to give the title product as an off-white solid (12.0 g, mp 161.5°–164.0° C.) which is identified by $^1$HNMR, $^{19}$FNMR and $^{13}$CNMR spectral analyses.

EXAMPLE 33

Preparation of 3-(p-Chlorophenyl)-2-(trifluoromethyl)thio]pyrrole

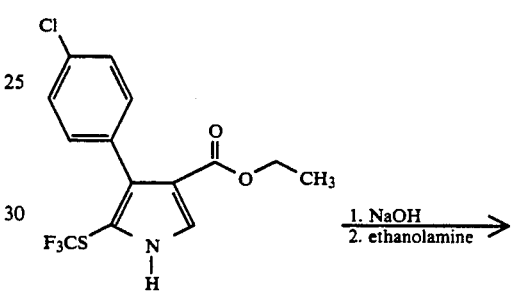

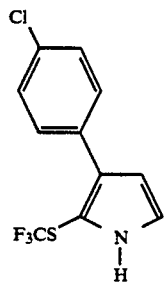

A solution of ethyl 4-(p-chlorophenyl)-5-[(trifluoromethyl)thio]pyrrole-3-carboxylate (8.0 g, 0.023 mol) in 10% aqueous sodium hydroxide solution is refluxed for several hours, stirred at room temperature overnight, poured into ice-water, treated with concentrated hydrochloric acid and extracted with ether. The combined organic extracts are washed with water and brine, dried over anhydrous magnesium sulfate and concentrated in vacuo to obtain a brown semi-solid. A solution of the semi-solid (6.9 g) in ethanolamine is heated at 110° C. for several hours, poured into ice-water and extracted with chloroform. The combined organic extracts are washed with water and brine, dried over anhydrous magnesium sulfate and concentrated in vacuo to give a brown oil. The oil is dissolved in methylene chloride, filtered through a bed of silica gel and the filtrate is concentrated in vacuo to obtain the title product as a grey semi-solid (4.8 g, mp 44°–46° C.) which is identified by $^1$HNMR spectral analysis.

EXAMPLE 34

Preparation of
2,3-Dibromo-4-(p-chlorophenyl)-5-[(trifluoromethyl)-thio]pyrrole

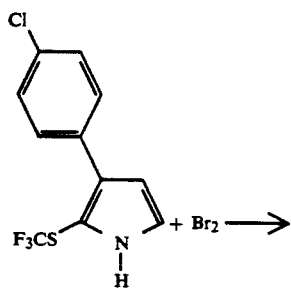

A solution of 3-(p-chlorophenyl)-2-[(trifluoromethyl)thio]pyrrole (3.0 g, 0.0108 mol) in methylene chloride (15 mL) is treated with bromine (4.0 g, 0.025 mol, 1.3 mL), stirred for one hour, washed with water and brine, dried over anhydrous magnesium sulfate and concentrated in vacuo to give the title product as a purple semi-solid (4.2 g) which is identified by $^1$HNMR and $^{13}$CNMR spectral analyses.

EXAMPLE 35

Preparation of
2,3-Dibromo-4-(p-chlorophenyl)-5-[(trifluoromethyl)-sulfinyl]pyrrole

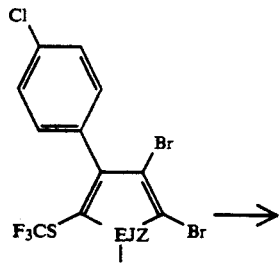

A solution of 2,3-dibromo-4-(p-chlorophenyl)-5-[(trifluoromethyl)thio]pyrrole (1.0 g, 0.0023 mol) in chloroform (10 mL) is treated with 3-chloroperoxybenzoic acid (0.4 g, 60%, 0.0023 mol) with stirring at 0° C., warmed to room temperature with stirring for two hours, washed with saturated sodium metabisulfite solution, saturated sodium hydrogen carbonate solution, water and brine, dried over anhydrous magnesium sulfate and concentrated in vacuo to obtain a yellow syrup. Flash chromatography of the syrup using silica gel and a 1:4 ethyl acetate/hexanes solution gives the title product as a yellow solid (0.4 g, mp 165.5°–167.5° C.) which is identified by $^1$NHMR, $^{19}$FNMR and $^{13}$CNMR spectral analyses.

EXAMPLE 36

Preparation of
2-(p-Chlorophenyl)-3-[(trifluoromethyl)sulfonyl]-5-[(trifluoromethyl)thio]pyrrole

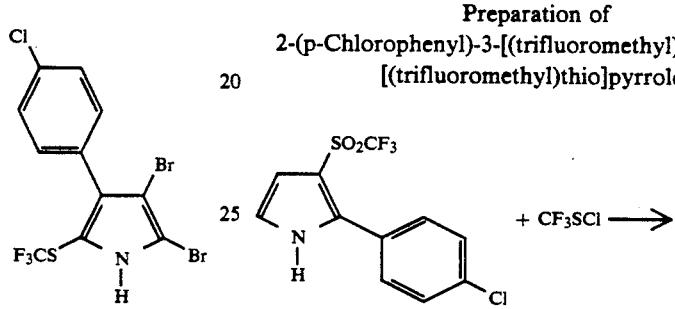

A solution of 2-(p-chlorophenyl)-3-[(trifluoromethyl)sulfonyl]pyrrole (2.47 g, 0.0080 mol), trifluoromethylsulfenyl chloride (2.18 g, 0.016 mol), trifluoromethanesulfonic acid (0.12 g, 0.0008 mol) and 1,2-dichloroethane (15 mL) is placed in a pressure tube, heated at 70° C. for five days, diluted with methylene chloride, washed with saturated sodium hydrogen carbonate solution and brine, dried over anhydrous magnesium sulfate and concentrated in vacuo to obtain an amber syrup. Flash chromatography of the syrup using silica gel and a 1:5 ethyl acetate/hexanes solution gives the title product as an off-white solid (2.36 g, mp 118°–122° C.) which is identified by $^1$HNMR and $^{13}$CNMR spectral analyses.

EXAMPLE 37

Preparation of
3,5-Bis[(trifluoromethyl)sulfonyl]-2-(p-chlorophenyl)-pyrrole

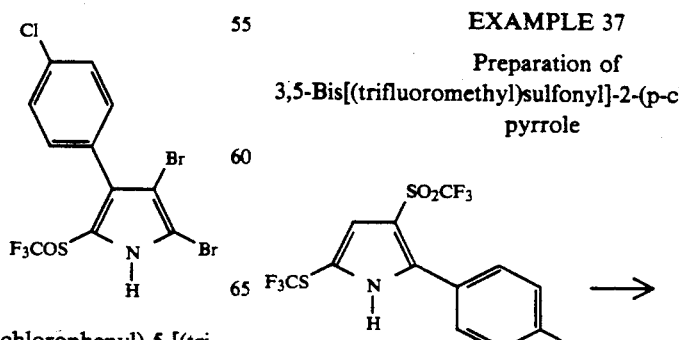

-continued

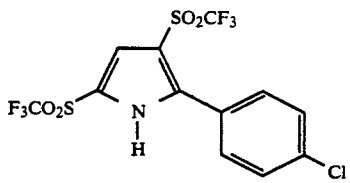

A solution of 2-(p-chlorophenyl)-3-[(trifluoromethyl)sulfonyl]-5-[(trifluoromethyl)thio]pyrrole (0.5 g, 0.00122 mol) in chloroform (20 mL) is cooled with an ice bath, treated with 3-chloroperoxybenzoic acid (0.81 g, 60% pure, 0.00281 mol), stirred for four hours, warmed to room temperature and stirred overnight. The reaction mixture is diluted with methylene chloride, washed sequentially with saturated sodium hydrogen carbonate solution and brine, dried over anhydrous magnesium sulfate and concentrated in vacuo to obtain a solid. Flash chromatography of the solid using silica gel and a 2:1 ethyl acetate/hexanes solution gives a solid which is recrystallized from carbon tetrachloride to obtain the title product as a white solid (0.23 g, mp 142°-144° C.) which is identified by $^1$HNMR spectral analysis.

EXAMPLE 38

Preparation of 3-Bromo-5-(p-chlorophenyl)-4-[(trifluoromethyl)sulfonyl]-2-[(trifluoromethyl)thiopyrrole

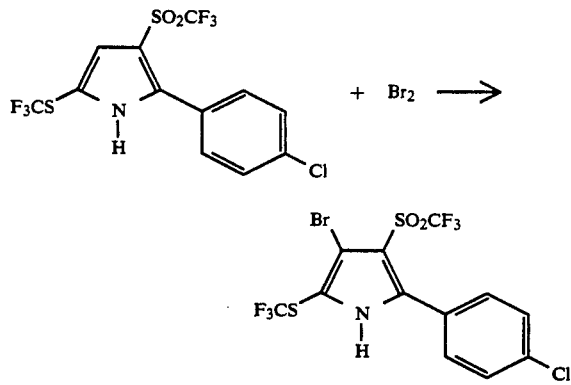

A solution of 2-(p-chlorophenyl)-3-[(trifluoromethyl)sulfonyl]-5-[(trifluoromethyl)thio]pyrrole (0.5 g, 0.00122 mol) in chloroform (10 mL) is cooled with an ice bath, treated with a solution of bromine (0.21 g, 0.00134 mol) in chloroform (5 mL), stirred for two hours, warmed to room temperature, treated with two drops of additional bromine and stirred for one hour. The reaction mixture is diluted with methylene chloride, washed with water, saturated sodium hydrogen carbonate solution, saturated sodium metabisulfite solution and brine, dried over anhydrous magnesium sulfate and concentrated in vacuo to obtain a syrup. Flash chromatography of the syrup using silica gel and a 1:5 ethyl acetate/hexanes solution gives the title product as a white solid (0.25 g, mp 122°-125° C.) which is identified by $^1$HNMR and $^{13}$CNMR spectral analyses.

EXAMPLE 39

Preparation of 3-Bromo-5-(p-chlorophenyl)-2-[(trifluoromethyl)sulfinyl]-4-[(trifluoromethyl)sulfonyl]pyrrole

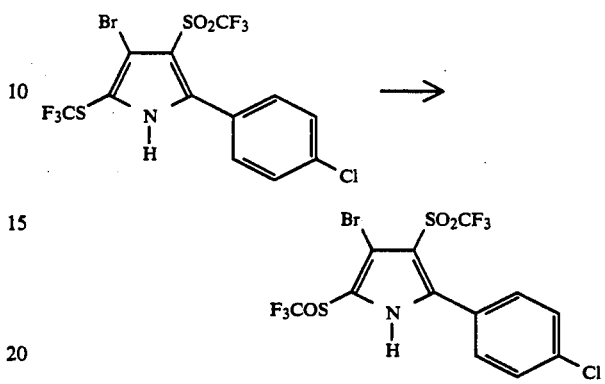

A solution of 3-bromo-5-(p-chlorophenyl)-4-[(trifluoromethyl)sulfonyl]-2-[(trifluoromethyl)thio]pyrrole (0.4 g, 0.00082 mol) in chloroform (5 mL) is cooled with an ice bath, treated with a solution of 3-chloroperoxybenzoic acid (0.24 g, 60%, 0.00082 mol) in chloroform (10 mL), stirred for two hours, warmed to room temperature and stirred overnight. The reaction mixture is treated with saturated sodium metabisulfite solution, diluted with methylene chloride, washed with saturated sodium hydrogen carbonate solution and brine, dried over anhydrous magnesium sulfate and concentrated in vacuo to obtain a residue. The residue is placed on a prep plate and eluted with a 1:2 ethyl acetate/hexanes solution to give the title product as a white solid (0.25 g, mp 120°-170° C.) which is $^1$HNMR spectral analysis.

Following the above procedure, but using at least two equivalents of 3-chloroperoxybenzoic acid yields 2,4-bis[(trifluoromethyl)sulfonyl]-3-bromo-5-(p-chlorophenyl)pyrrole, mp 115°-135° C.

EXAMPLE 40

Preparation of Ethyl 5-(p-chlorophenyl)-4-thiocyanatopyrrole-2-carboxylate

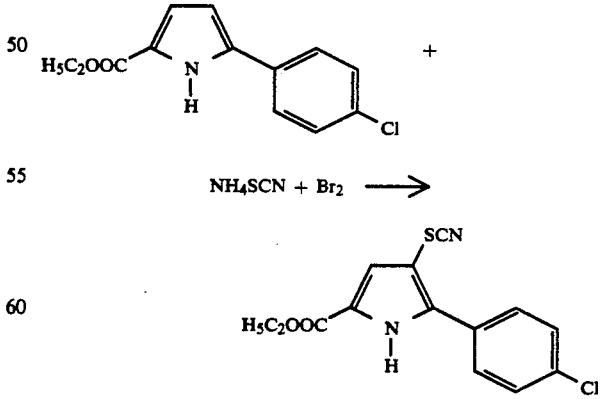

A solution of ethyl 5-(p-chlorophenyl)pyrrole-2-carboxylate (0.95 g, 3.8 mmol) in acetic acid (20 mL) is treated with ammonium thiocyanate (1.75 g, 22.8 mmol), stirred at room temperature for five minutes, cooled to 15° C., treated with a solution of bromine (0.91 g, 5.7 mmol) in acetic acid (10 mL) and stirred at room temperature for several hours. The reaction mixture is filtered to remove solids and the filtrate is poured into water and stirred. The aqueous mixture is filtered to obtain an off-white solid. Flash chromatography of the solid using a 1:10 ethyl acetate/hexanes solution gives the title product as a white solid (0.99 g, mp 138°-141° C.) which is identified by ¹HNMR and ¹³CNMR spectral analyses.

EXAMPLE 41

Preparation of Ethyl 5-(p-chlorophenyl)-4-[(difluoromethyl)thio]pyrrole-2-carboxylate

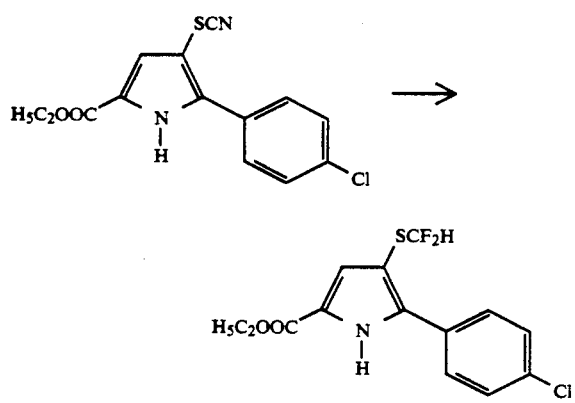

A solution of ethyl 5-(p-chlorophenyl)-4-thiocyanatopyrrole-2-carboxylate (76.7 mg, 0.25 mmol) in 2-propanol is treated with sodium borohydride (11.0 mg, 0.29 mmol) under nitrogen, heated to 70° C. for ten minutes, cooled to room temperature, treated with a solution of potassium hydroxide (16.8 mg, 0.30 mmol) in 2-propanol, treated with tributylphosphine (81.2 mg, 0.4 mmol), heated to 65°-70° C. and treated with excess chlorodifluoromethane for one hour. Additional tributylphosphine (81.2 mg, 0.4 mmol) is added to the reaction mixture and the addition of chlorodifluoromethane is continued for 30 minutes. The mixture is then poured into brine and extracted with ethyl acetate. The combined organic extracts are washed with water, dried over anhydrous sodium sulfate and concentrated in vacuo to obtain a liquid. Flash chromatography of the liquid using silica gel and a 1:10 ethyl acetate/hexanes solution gives the title product as a white solid (42.6 mg, mp 113°-117° C.) which is identified by ¹HNMR and ¹³CNMR spectral analyses.

Following the above procedure, but substituting tetrafluoroethylene for chlorodifluoromethane yields ethyl 5-(p-chlorophenyl)-4-[(1,1,2,2-tetrafluoroethyl)thio]pyrrole-2-carboxylate.

EXAMPLE 42

Preparation of 5-(p-Chlorophenyl)-4-[(difluoromethyl)thio]pyrrole-2-carboxylic acid

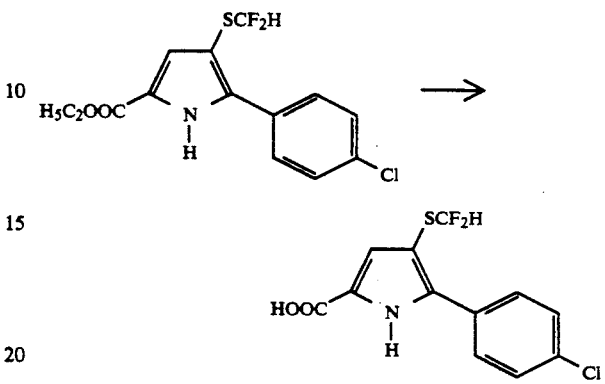

A solution of ethyl 5-(p-chlorophenyl)-4-[(difluoromethyl)thio]pyrrole-2-carboxylate (166 mg, 0.5 mmol) in ethanol is treated under nitrogen with a solution of sodium hydroxide (100 mg, 2.5 mmol) in water. The reaction mixture is refluxed for three hours, poured into ice-water, treated with hydrochloric acid and extracted with ethyl acetate. The combined organic extracts are washed with water and brine, dried over anhydrous sodium sulfate and concentrated in vacuo to obtain the title product as an orange solid (158 mg, mp 165° C. (dec)) which is identified by ¹HNMR and ¹³CNMR spectral analyses.

EXAMPLE 43

Preparation of 2,3-Dibromo-5-(p-chlorophenyl)-4-[(difluoromethyl)thio]pyrrole

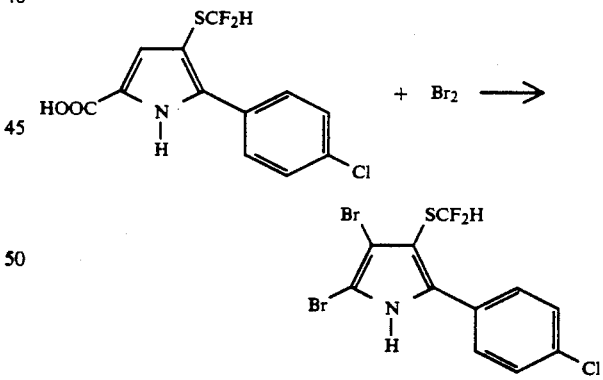

A solution of 5-(p-chlorophenyl)-4-[(difluoromethyl)thio]pyrrole-2-carboxylic acid (5.39 g, 0.0178 mol) and sodium acetate (6.4 g, 0.0781 mol) in acetic acid is treated with a solution of bromine (6.24 g, 0.039 mol) in acetic acid under nitrogen. The reaction mixture is stirred for three hours at room temperature, poured into ice-water and extracted with ethyl acetate. The combined organic extracts are washed with water, saturated sodium hydrogen carbonate solution and brine, dried over anhydrous sodium sulfate and concentrated in vacuo to obtain a red gum. A mixture of the gum, ethyl acetate and silica gel is evaporated to dryness and placed on a column packed with silica gel. The column is eluted with a 1:10 ethyl acetate/hexanes solution to obtain a gum. The gum is dissolved in ethyl acetate, treated with carbon black, filtered through celite and concentrated in vacuo to obtain an orange gum. The orange gum is dissolved in an ether/pentane solution, cooled to 0° C. and filtered to remove solids. After the filtrate is concentrated in vacuo, the residue is dissolved in acetone, treated with carbon black, filtered through celite and concentrated in vacuo to give the title product as a red gum (4.33 g) which is identified by $^1$HNMR spectral analysis.

EXAMPLE 44

Preparation of
2,3-Dibromo-5-(p-chlorophenyl)-4-[(difluoromethyl)-sulfinyl]pyrrole

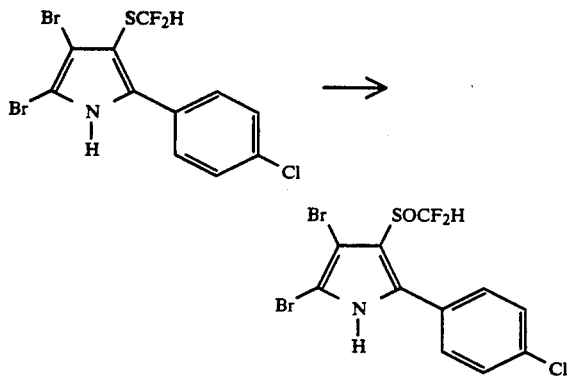

A solution of 2,3-dibromo-5-(p-chlorophenyl)-4-[(difluoromethyl)thio]pyrrole (125 mg, 0.030 mmol) in chloroform is treated with 3-chloroperoxybenzoic acid (86 mg, 60%, 0.30 mmol) at 0° C. The reaction mixture is stirred for one hour at 0° C., warmed to room temperature, stirred overnight, poured into saturated sodium metabisulfite solution and diluted with a methylene chloride/water mixture. The organic phase is separated, washed with saturated sodium hydrogen carbonate solution, dried over anhydrous sodium sulfate and concentrated in vacuo to obtain a residue. Flash chromatography of the residue using silica gel and a 1:10 ethyl acetate/hexanes solution gives the title product as a yellow solid (68 mg, mp 180° C. (dec)) which is identified by $^1$HNMR and $^{13}$CNMR spectral analyses.

EXAMPLE 45

Preparation of
2-(p-Chlorophenyl)-5-(trifluoromethyl)-3-[(trifluoromethyl)thio]pyrrole

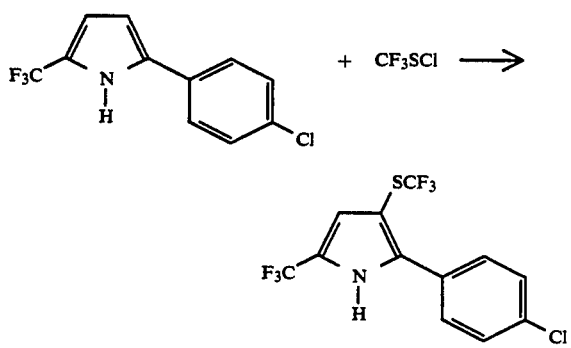

A solution of 2-(p-chlorophenyl)-5-(trifluoromethyl)-pyrrole (11.2 g, 45.7 mmol) in methylene chloride is treated with an excess of trifluoromethylsulfenyl chloride, stirred overnight at room temperature, treated with trifluoromethanesulfonic acid (40 drops) and additional trifluoromethylsulfenyl chloride, stirred for 30 minutes and diluted with an ether/water mixture. The organic phase is separated, washed with water, dried over anhydrous magnesium sulfate and concentrated in vacuo to obtain a purple oil. Flash chromatography of the oil using silica gel and a 1:9 ethyl acetate/hexanes solution gives a blue oil which is crystallized from petroleum ether to obtain the title product as a purple solid (mp 53°–55.0° C.) which is identified by $^1$HNMR and $^{13}$CNMR spectral analyses.

EXAMPLE 46

Preparation of
3-Bromo-5-(p-chlorophenyl)-2-(trifluoromethyl)-4-[(trifluoromethyl)thiopyrrole

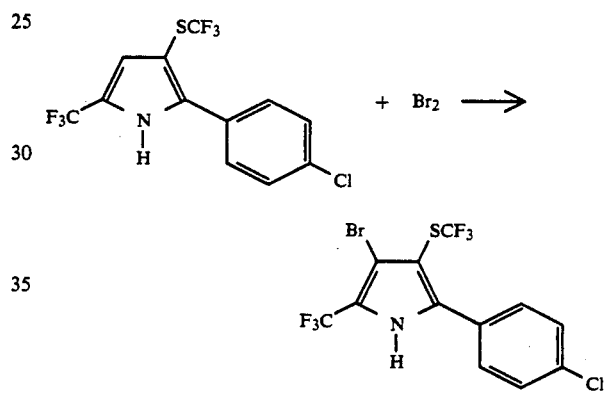

A solution of 2-(p-chlorophenyl)-5-(trifluoromethyl)-3-[(trifluoromethyl)thio]pyrrole (1.03 g, 3.0 mmol) and sodium acetate (0.3 g, 3.6 mmol) in acetic acid is treated with bromine (0.58 g, 3.6 mmol), stirred for 30 minutes at room temperature and diluted with an ethyl acetate/water mixture. The organic phase is separated, washed with water, dried over anhydrous magnesium sulfate and concentrated in vacuo to obtain a semi-solid. Chromatography of the semi-solid using silica gel and hexanes gives the title product as a white solid (mp 87°–88.5° C.) which is identified by $^1$HNMR, $^{19}$FNMR and $^{13}$CNMR spectral analyses.

EXAMPLE 47

Preparation of
2-(p-Chlorophenyl)-5-(trifluoromethyl)-3-[(trifluoromethyl)sulfinyl]pyrrole

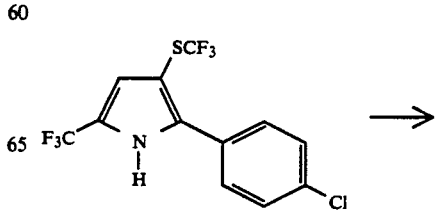

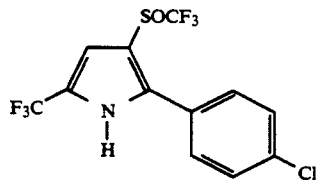

A solution of 2-(p-chlorophenyl)-5-(trifluoromethyl)-3-[(trifluoromethyl)thio]pyrrole (5.5 g, 5.9 mmol) in chloroform is cooled to 0° C., treated with 3-chloroperoxybenzoic acid (5.49 g, 60%, 19.1 mmol), stirred for several hours and filtered to remove solids. The solids are dissolved into ether and the organic solution is washed with water and saturated sodium hydrogen carbonate solution, dried over anhydrous magnesium sulfate and concentrated in vacuo to obtain a solid. Recrystallization of the solid from ether gives the title product as a white solid (mp 98°-200° C.) which is identified by $^1$HNMR, $^{19}$FNMR and $^{13}$CNMR spectral analyses.

EXAMPLE 48

Preparation of 2-(p-Chlorophenyl)-5-(trifluoromethyl)3-[(trifluoromethyl)sulfonyl]pyrrole

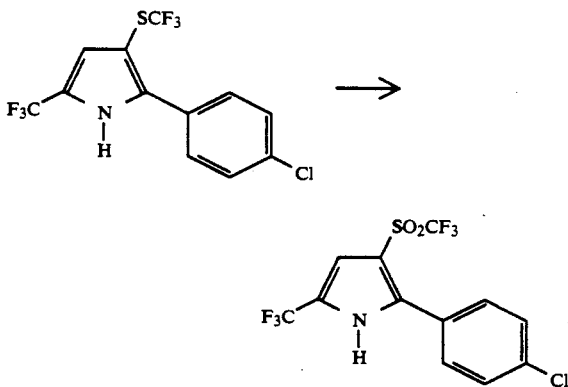

A solution of 2-(p-chlorophenyl)-5-(trifluoromethyl)-3-[(trifluoromethyl)thio]pyrrole (1.5 g, 4.3 mmol) in acetic acid is treated with hydrogen peroxide (1.5 mL, 30%, 13 mmol), stirred at 95° C. for several hours, treated with additional hydrogen peroxide (1 mL), stirred at 90° C. for four hours, cooled to room temperature, stirred for 48 hours, treated with additional hydrogen peroxide (1 mL), stirred for several hours at reflux, cooled and diluted with an ethyl acetate/water mixture. The organic phase is separated, dried over anhydrous magnesium sulfate and concentrated in vacuo to obtain an oil. Crystallization of the oil from petroleum ether gives a white semi-solid which is chromatographed using silica gel and a 1:9 ethyl acetate/hexanes solution to obtain the title product as a white solid (mp 167°-169° C.) which is identified by $^1$HNMR, $^{19}$FNMR and $^{13}$CNMR spectral analyses.

EXAMPLE 49

Preparation of 3-Bromo-5-(p-chlorophenyl)-1-(ethoxymethyl)-2-(trifluoromethyl)-4-[(trifluoromethyl)thio]pyrrole

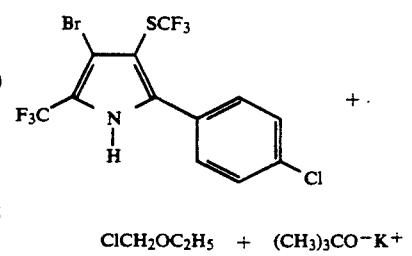

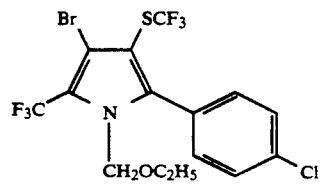

A solution of 3-bromo-5-(p-chlorophenyl)-2-(trifluoromethyl)-4-[(trifluoromethyl)thio]pyrrole (0.6 g, 1.4 mmol) and potassium tert-butoxide (0.19 g, 1.7 mmol) in tetrahydrofuran is stirred for 15 minutes, treated with chloromethyl ethyl ether (0.16 g, 1.7 mmol), stirred for 30 minutes and diluted with an ether/water mixture. The organic phase is separated, dried over anhydrous magnesium sulfate and concentrated in vacuo to obtain a residue. Chromatography of the residue using silica gel and a 1:9 ethyl acetate/hexanes solution gives the title product as an amber oil which is identified by $^1$HNMR and $^{13}$CNMR spectral analyses.

Following the above procedure, but substituting 2-(p-chlorophenyl)-5-(trifluoromethyl)-3-[(trifluoromethyl)sulfinyl]pyrrole for 3-bromo-5-(p-chlorophenyl)- 2-(trifluoromethyl)-4-[(trifluoromethyl)thio]pyrrole yields 2-(p-chlorophenyl)-1-(ethoxymethyl)-5-(trifluoromethyl)-3-[(trifluoromethyl)sulfinyl]pyrrole as an oil.

EXAMPLE 50

Preparation of 2-(p-Chlorophenyl)-4-phenyl-5-(trifluoromethyl)-3-(trifluoromethyl)sulfonyl]pyrrole

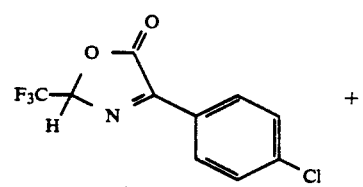

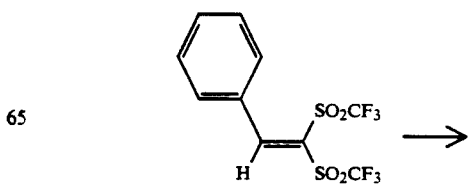

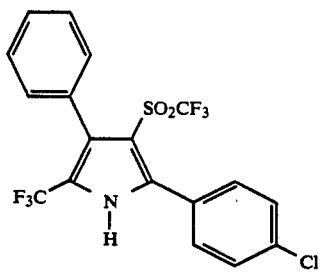

A solution of 4-(p-chlorophenyl)-2-(trifluoromethyl)-3-oxazolin-5-one (1.0 g, 3.8 mmol) and b,b-bis[(trifluoromethyl)sulfonyl]styrene (1.4 g, 3.8 mmol) in dimethylformamide is stirred for two hours at 110° C., treated with triethylamine (0.38 g, 3.8 mmol), stirred for several hours at reflux and diluted with an ethyl acetate/water mixture. The organic phase is separated, washed with water and dilute hydrochloric acid, dried over anhydrous magnesium sulfate and concentrated in vacuo to obtain a residue. Chromatography of the residue using silica el and a 1:10 ethyl acetate/hexanes solution gives the title product as an amber oil which is identified by $^1$HNMR and $^{13}$CNMR spectral analyses.

EXAMPLE 51

Preparation of Trifluoromethyl 1-chloro-N-(p-chlorothioformimidate

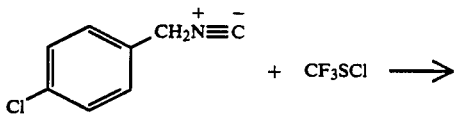

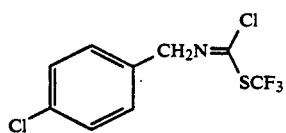

Trifluoromethylsulfenyl chloride (4.0 g, 0.03 mol) is bubbled over 30 minutes into a solution of 4-chlorobenzylisonitrile (3.0 g, 0.02 mol) in methylene chloride, causing the formation of a white precipitate. The suspension is stirred for 16 hours at room temperature and filtered to remove solids. The white filter cake is washed with methylene chloride and solvent is removed under reduced pressure to obtain an amber oil. Bulb-to-bulb distillation of the oil (90°-100° C., 0.05 mmHg) gives the title product as a colorless oil (3.9 g, 68%).

EXAMPLE 52

Preparation of 2-(p-Chlorophenyl)-5-[(trifluoromethyl)thio]pyrrole-3-carbonitrile

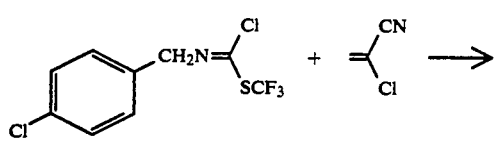

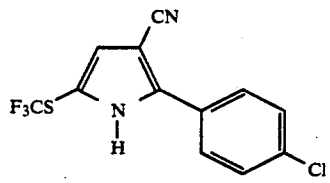

Under a nitrogen purge, a solution of trifluoromethyl-1-chloro-N-(p-chlorobenzyl)thioformimidate (1.1 g, 0.004 mol) and 2-chloroacrylonitrile (0.4 mL, 0.005 mol) is treated with a solution of triethylamine (1.3 mL, 0.009 mol) in toluene. After an induction period, solids begin to form as the reaction mixture exotherms slightly. When the exotherm subsides, the reaction mixture is heated at reflux temperature for 16 hours, cooled and filtered. The filter cake is washed with ethyl acetate and the filtrate is concentrated in vacuo to obtain a semi-solid. The semi-solid is dissolved in ethyl acetate and the organic solution is washed with water and brine, dried over anhydrous magnesium sulfate and concentrated in vacuo to obtain a solid. The solid is twice recrystallized from 1,2-dichloroethane to give the title product as a beige solid (0.7 g, mp 203°-205° C.) which is identified by $^1$HNMR spectral analysis.

EXAMPLE 53

Preparation of 2-(p-Chlorophenyl)-5-[(trifluoromethyl)sulfonyl]pyrrole-3-carbonitrile

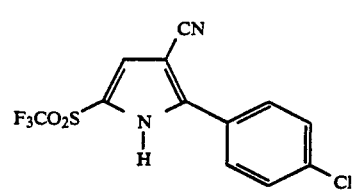

A solution of 2-(p-chlorophenyl)-5-[(trifluoromethyl)thio]pyrrole-3-carbonitrile (0.6 g, 0.002 mol) in acetic acid is treated portionwise with 30% hydrogen peroxide solution (0.6 mL, 0.006 mol), stirred for 1½ hours at 90° C., treated with additional hydrogen peroxide (0.3 mL, 0.003 mol), stirred for two hours at 90° C., stirred for 16 hours at room temperature and diluted with an ethyl acetate/water mixture. The organic phase is separated, washed with water and brine, dried over anhydrous magnesium sulfate and concentrated in vacuo to obtain a solid. The solid is recrystallized from ethylene dichloride to give the title product as a beige solid (mp 228°-230° C.) which is identified by $^1$HNMR and $^{13}$CNMR spectral analyses.

EXAMPLE 54

Preparation of 4-Bromo-2-(p-chlorophenyl)-5-[(trifluoromethyl)thio]-pyrrole-3-carbonitrile

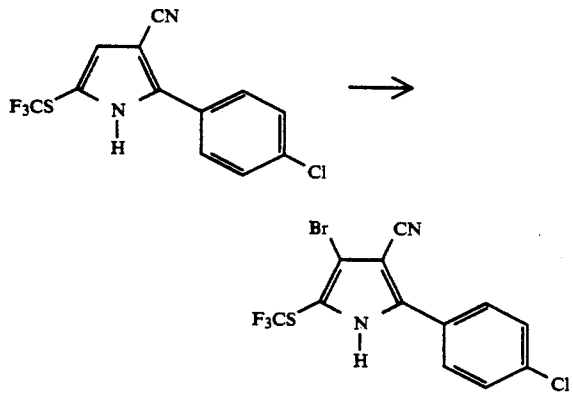

Under a nitrogen purge, a solution of 2-(p-chlorophenyl)-5-[(trifluoromethyl)thio]pyrrole-3-carbonitrile (0.6 g, 0.002 mol) in tetrahydrofuran is treated with N-bromosuccinimide (0.36 g, 0.002 mol), stirred for 16 hours at room temperature and concentrated in vacuo to obtain a residue. The residue is dissolved in ether and diluted with water. The organic phase is separated, washed with water and brine, dried over anhydrous magnesium sulfate and concentrated in vacuo to obtain a solid. High performance liquid chromatography indicates that the solid contains 20% starting material. A solution of the mixture and sodium acetate (0.05 g, 0.006 mol) in acetic acid is treated with bromine (0.03 mL, 0.0006 mol), stirred for 16 hours at 60° C., cooled and concentrated in vacuo to obtain a semi-solid. The semi-solid is partitioned between ethyl acetate and water. The organic phase is separated, washed with water and brine, dried over anhydrous magnesium sulfate and concentrated in vacuo to obtain a solid. The solid is recrystallized from ethylene dichloride to give the title product as an off-white solid (mp 241°–243° C.) which is identified by $^1$HNMR and $^{13}$CNMR spectral analyses.

EXAMPLE 55

Preparation of 3-(p-Chlorophenyl)-1-methyl-4-[(trifluoromethyl)sulfonyl]pyrrole

H$_3$C—N—CH$_2$COOH +
  |
  CHO

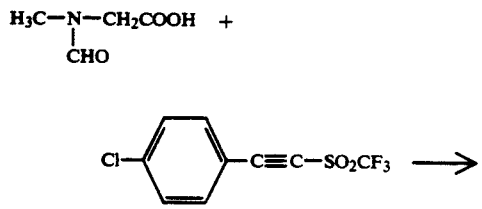

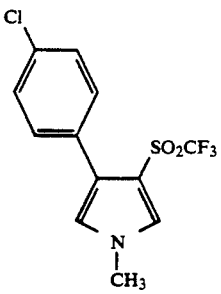

A solution of 2-(p-chlorophenyl)ethynyl trifluoromethylsulfone (4.8 g, 0.018 mol) and N-formylsarcosine (2.9 g, 0.025 mol) in acetic anhydride is stirred for three hours at reflux temperature, stirred overnight at room temperature, concentrated in vacuo, diluted with water and extracted with ether. The combined organic extracts are concentrated in vacuo to obtain a residue. Flash chromatography of the residue using silica gel and a 1:3 ethyl acetate/hexanes solution gives a brown solid which is recrystallized from a benzene/hexanes solution to obtain the title product as a white solid (1.9 g, mp 70°–73° C.) which is identified by $^1$HNMR and $^{13}$CNMR spectral analyses.

EXAMPLE 56

Preparation of 2-Chloro-3-(p-chlorophenyl)-1-methyl-4-[(trifluoromethyl)sulfonyl]pyrrole

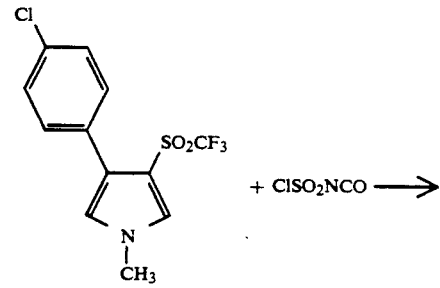

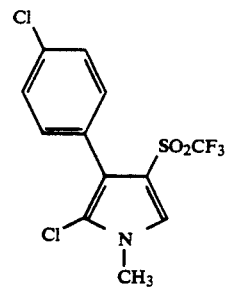

A solution of 3-(p-chlorophenyl)-1-methyl-4-[(trifluoromethyl)sulfonyl]pyrrole (0.5 g, 0.0015 mol) in dimethoxyethane is treated with chlorosulfonyl isocyanate (0.3 mL, 0.0034 mol), stirred for 24 hours at room temperature, treated with additional chlorosulfonyl isocyanate (0.6 mL, 0.0068 mol), stirred for 24 hours, treated with dimethylformamide (2 mL), stirred for one hour, diluted with water and extracted with ether. The combined organic extracts are washed with water, dried and concentrated in vacuo to obtain a semi-solid. Flash chromatography of the semi-solid using silica gel and a 1:4 ethyl acetate/hexanes solution gives the title product as a white solid (0.2 g, mp 117°–119° C.) which is identified by $^1$HNMR and $^{13}$CNMR spectral analyses.

EXAMPLE 57

Preparation of Ethyl 5-(p-chlorophenyl)-4-[(1,1,2,2-tetrafluoroethyl)sulfonyl]pyrrole-2-carboxylate and Ethyl 5-(p-chlorophenyl)-4-[(1,1,2,2-tetrafluoroethyl)sulfinyl]pyrrole-2-carboxylate

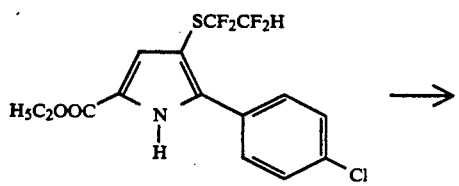

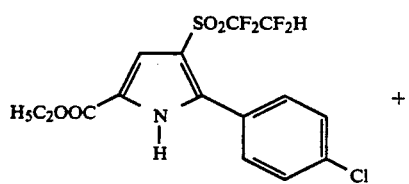

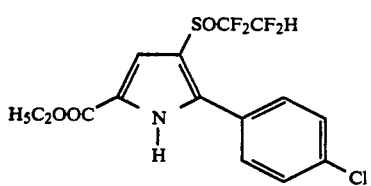

A solution of ethyl 5-(p-chlorophenyl)-4-[(1,1,2,2-tetrafluoroethyl)thio]pyrrole-2-carboxylate (1.83 g, 0.0022 mol) in chloroform is cooled with an ice bath, treated with 3-chloroperoxybenzoic acid (3.2 g, 0.011 mol), stirred for one hour, warmed to room temperature, stirred for several hours, cooled with an ice bath, treated with additional 3-chloroperoxybenzoic acid (2.7 g, 60%, 0.009 mol), stirred for several hours, treated with saturated sodium metabisulfite solution and diluted with a methylene chloride/water mixture. The organic phase is separated, washed with saturated sodium hydrogen carbonate solution, dried over anhydrous sodium sulfate and concentrated in vacuo to obtain a residue. Flash chromatography of the residue using silica gel and a 1:5 ethyl acetate/hexanes solution gives ethyl 5-(p-chlorophenyl)-4-[(1,1,2,2-tetrafluoroethyl)sulfonyl]pyrrole-2-carboxylate as a white solid (0.54 g, 153°–156° C.) and ethyl 5-(p-chlorophenyl)-4-[(1,1,2,2-tetrafluoroethyl)sulfinyl]pyrrole-2-carboxylate as a white solid (1.28 g, mp 138°–140° C.). Both products are identified by $^1$HNMR and $^{13}$CNMR spectral analyses.

EXAMPLE 58

Preparation of 5-(p-Chlorophenyl)-4-[(1,1,2,2-tetrafluoroethyl)sulfonyl]pyrrole-2-carboxylic acid

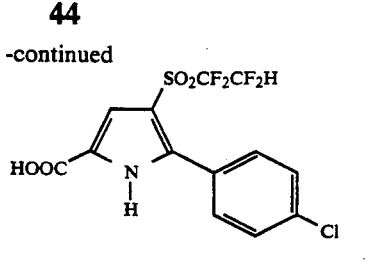

A solution of ethyl 5-(p-chlorophenyl)-4-[(1,1,2,2-tetrafluoroethyl)sulfonyl]pyrrole-2-carboxylate (0.54 g, 0.0012 mol) in ethanol is treated under nitrogen with a solution of sodium hydroxide (0.26 g, 0.0065 mol) in water. The reaction mixture is refluxed for three hours, poured into ice-water, treated with hydrochloric acid and extracted with ethyl acetate. The combined organic extracts are washed with water and brine, dried over anhydrous sodium sulfate and concentrated in vacuo to obtain the title product as a gum (0.6 g).

EXAMPLE 59

Preparation of 2,3-Dibromo-5-(p-chlorophenyl)-4-[(1,1,2,2-tetrafluoroethyl)sulfonyl]pyrrole

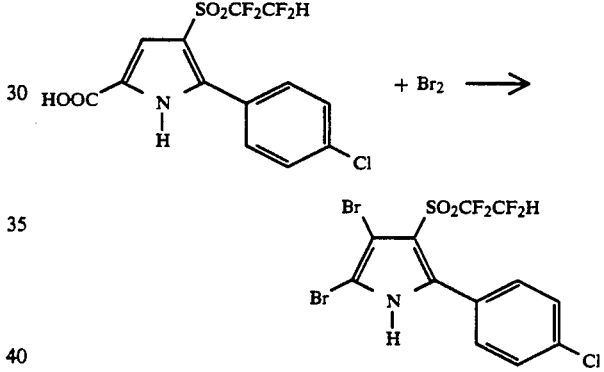

A solution of 5-(p-chlorophenyl)-4-[(1,1,2,2-tetrafluoroethyl)sulfonyl]pyrrole-2-carboxylic acid (0.5 g, 0.0013 mol) and sodium acetate (0.47 g, 0.0057 mol) in acetic acid is treated with a solution of bromine (0.46 g, 0.0029 mol) in acetic acid, stirred for two hours at 60° C., poured into ice-water and extracted with ethyl acetate. The combined organic extracts are washed with water, saturated sodium hydrogen carbonate solution and brine, dried over anhydrous sodium sulfate and concentrated in vacuo to obtain a red gum. Flash chromatography of the gum using silica gel and a 1:6 ethyl acetate/hexanes solution gives the title product as a pale green solid (0.37 g, mp 138°–141° C.) which is identified by $^1$HNMR and $^{13}$CNMR spectral analyses

EXAMPLE 60

In vivo evaluation of test compounds as fungicidal agents

Compounds are dissolved in acetone, diluted to the desired concentration with water and surfactant and sprayed onto the test plants. After drying, the test plants are treated with fungal inoculum. When disease symptom development is optimal, plants are rated for disease control Inoculated untreated plants, solvent/surfactant treated plants and plants treated with a reference standard are used for comparison.

| Test Organisms | |
|---|---|
| Common Name | Scientific Name |
| Apple scab | *Venturia inaequalis* |
| Grape downy mildew | *Plasmopara viticola* |
| Wheat powdery mildew | *Erysiphe graminis f. sp. tritici* |

Compounds are rated for control of each disease according to the rating scale shown below.

| Rating | % Control of Disease |
|---|---|
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |
| P | Phytotoxic |

The results are reported in Table I.

TABLE I

| | In Vivo Fungicidal Evaluations | | |
|---|---|---|---|
| Compound | Apple Scab (400 ppm) | Grape Downy Mildew (400 ppm) | Wheat Powdery Mildew (400 ppm) |
| 2,3-Dichloro-5-(p-chlorophenyl)-4-[(trifluoromethyl)sulfonyl]pyrrole | P | P | 5 |
| 2-Phenyl-3-[(trifluoromethyl)sulfonyl]pyrrole | 4 | 0 | 0 |
| 2,3-Dibromo-4-[(trifluoromethyl)sulfonyl]-5-(alpha,alpha,alpha-trifluoro-p-tolyl)pyrrole | P | 9 | 2 |
| 2,3-Dibromo-5-(p-chlorophenyl)-1-(ethoxymethyl)-4-[(trifluoromethyl)sulfonyl]pyrrole | 0 | 0 | 8 |
| 2,3-Dibromo-5-(p-tert-butylphenyl)-4-[(trifluoromethyl)sulfonyl]pyrrole | 7 | 8 | 0 |
| 2,3-Dibromo-1-(chloromethyl)-5-(p-chlorophenyl)-4-[(trifluoromethyl)sulfonyl]pyrrole | 0 | 2 | 0 |
| 3-[(Trifluoromethyl)sulfonyl]-2-(alpha,alpha,alpha-trifluoro-p-tolyl)pyrrole | 6 | 9 | 7 |
| 5-(p-Bromophenyl)-2,3-dichloro-4-[(trifluoromethyl)sulfonyl]pyrrole | P | 9 | 4 |
| 2-(p-tert-butylphenyl)-3-[(trifluoromethyl)sulfonyl]pyrrole | 5 | 7 | 0 |
| 3-Bromo-5-(p-chlorophenyl)-4-[(trifluoromethyl)sulfonyl]pyrrole-2-carbonitrile | 0 | 6 | 4 |
| {2,3-Dibromo-5-(p-chlorophenyl)-4-[(trifluoromethyl)sulfonyl]pyrrol-1-yl}methyl dimethyldithiocarbamate | 0 | 4 | 0 |
| 3,4-Dibromo-2-(p-chlorophenyl)-5-[(trifluoromethyl)thio]pyrrole | 4 | 6 | 4 |
| 2-(3,4-Dichlorophenyl)-3-[(trifluoromethyl)sulfonyl]pyrrole | 6 | 6 | 0 |
| {2,3-Dibromo-5-(p-chlorophenyl)-4-[(trifluoromethyl)sulfonyl]pyrrol-1-yl}methyl p-toluate | 6 | 5 | 0 |
| {2,3-Dibromo-5-(p-chlorophenyl)-4-[(trifluoromethyl)sulfonyl]pyrrol-1-yl}methyl p-chlorohippurate | 0 | 7 | 0 |
| 2,3-Dibromo-5-(3,4-dichlorophenyl)-4-[(trifluoromethyl)sulfonyl]pyrrole | 6 | 9 | P |
| 3,4-Dibromo-2-(p-chlorophenyl)-5-[(trifluoromethyl)sulfinyl]pyrrole | P | 0 | 4 |
| 3-Bromo-2-(p-chlorophenyl)-5-[(trifluoromethyl)sulfinyl]pyrrole | 0 | 3 | 4 |
| 2-(p-chlorophenyl)-4-phenyl-5-(trifluoromethyl)-3-[(trifluoromethyl)sulfonyl]pyrrole | 8 | 7 | 6 |
| 2-p-Tolyl-3-[(trifluoromethyl)sulfonyl]pyrrole | 6 | 6 | 0 |
| 2,3-Dichloro-5-(3,4-dichlorophenyl)-4-[(trifluoromethyl)sulfonyl]pyrrole | 7 | 7 | P |
| 2-(p-Chlorophenyl)-5-[(trifluoromethyl)thio]pyrrole-3-carbonitrile | 7 | 8 | 9 |
| 2,3-Dibromo-5-p-tolyl-4-[(trifluoromethyl)sulfonyl]pyrrole | 7 | 8 | 0 |
| p-{2,3-Dibromo-4-[(trifluoromethyl)sulfonyl]pyrrol-2-yl}benzonitrile | P | 5 | P |
| p-{5-Bromo-3-[(trifluoromethyl)sulfonyl]pyrrol-2-yl}benzonitrile | P | 8 | 0 |
| 2,5-Dibromo-3-(p-chlorophenyl)- | 0 | 6 | 0 |

TABLE I-continued

| Compound | In Vivo Fungicidal Evaluations | | |
|---|---|---|---|
| | Apple Scab (400 ppm) | Grape Downy Mildew (400 ppm) | Wheat Powdery Mildew (400 ppm) |
| 4-[(trifluoromethyl)sulfonyl]pyrrole | | | |
| 2-Bromo-3-(p-chlorophenyl)-4-[(trifluoromethyl)sulfonyl]pyrrole | 8 | 8 | 0 |
| 3-(p-Chlorophenyl)-4-[(trifluoromethyl)sulfonyl]pyrrole | 7 | 7 | 0 |
| 2-(p-Chlorophenyl)-5-[(difluoromethyl)thio]pyrrole | 0 | 7 | 2 |
| 3,4-Dibromo-2-(p-chlorophenyl)-5-[(difluoromethyl)thio]pyrrole | 0 | 8 | 2 |
| 2,3-Dichloro-5-p-tolyl-4-[(trifluoromethyl)sulfonyl]pyrrole | 8 | 9 | 4 |

EXAMPLE 61

In vitro evaluation of test compounds as fungicidal agents

Test compounds are dissolved in acetone to achieve a concentration of 10,000 ppm. Five microliters of each solution is then added to individual cell wells containing 2 mL/well of a nutrient medium and fungal mycelium suspension to obtain a final test compound concentration of 25 ppm. The cell wells are incubated under ambient laboratory conditions for three days and growth inhibition of the fungus is rated. Untreated cell wells and wells treated with a solvent blank and reference standard are used for comparison.

| Test Organisms | |
|---|---|
| Header | Scientific Name |
| PYTHUL | *Pythium ultimum* |
| RHIZSO | *Rhizoctonia solani* |

Compounds are rated for fungal growth inhibition according to the rating scale shown below.

| Rating | Inhibition |
|---|---|
| 0 | No inhibition |
| 3 | Slight inhibition |
| 5 | Moderate inhibition |
| 7 | Severe inhibition |
| 9 | Complete inhibition |

The results are reported in Table II.

TABLE II

| Compound | In Vitro Fungicidal Evaluations | |
|---|---|---|
| | PYTHUL (25 ppm) | RHIZSO (25 ppm) |
| 2,3-Dichloro-5-(p-chlorophenyl)-4-[(trifluoromethyl)sulfonyl]pyrrole | 9 | 9 |
| 5-(p-Chlorophenyl)-4-[(trifluoromethyl)sulfonyl]pyrrole-2-carbonitrile | 9 | 9 |
| 2-Phenyl-3-[(trifluoromethyl)sulfonyl]pyrrole | 5 | 0 |
| 2,3-Dibromo-5-phenyl-4-[(trifluoromethyl)sulfonyl]pyrrole | 9 | 9 |
| 2,3-Dibromo-4-[(trifluoromethyl)sulfonyl]-5-(a,a,a-trifluoro-p-tolyl)pyrrole | 9 | 9 |
| 2,3-Dibromo-5-(p-tert-butylphenyl)-4-[(trifluoromethyl)sulfonyl]pyrrole | 3 | 0 |
| 2,3-Dibromo-1-(chloromethyl)-5-(p-chlorophenyl)-4-[(trifluoromethyl)sulfonyl]pyrrole | 3 | 0 |
| 3-[(Trifluoromethyl)sulfonyl]-2-(a,a,a-trifluoro-p-tolyl)-pyrrole | 5 | 0 |
| 5-(p-Bromophenyl)-2,3-dichloro-4-[(trifluoromethyl)sulfonyl]pyrrole | 9 | 9 |
| 3-Bromo-5-(p-chlorophenyl)-4-[(trifluoromethyl)sulfonyl]pyrrole-2-carbonitrile | 9 | 0 |
| 2-(3,4-Dichlorophenyl)-3-[(trifluoromethyl)sulfonyl]pyrrol | 5 | 5 |
| 2,3-Dibromo-5-(3,4-dichlorophenyl)-4-[(trifluoromethyl)sulfonyl]pyrrole | 9 | 7 |
| 3-Bromo-2-(p-chlorophenyl)-5-[(trifluoromethyl)sulfonyl]pyrrole | 0 | 7 |
| 3-Bromo-2-(p-chlorophenyl)-5-[(trifluoromethyl)sulfinyl]pyrrole | 0 | 7 |
| 3-Bromo-2-(p-chlorophenyl)-5-[(trifluoromethyl)thio]pyrrole | 0 | 9 |
| 2-(p-Chlorophenyl)-4-phenyl-5-(trifluoromethyl)-3-[(trifluoromethyl)sulfonyl]pyrrole | 5 | 5 |
| 2-p-Tolyl-3-[(trifluoromethyl)sulfonyl]pyrrole | 5 | 0 |
| 2,3-Dichloro-5-(3,4-dichlorophenyl)-4-[(trifluoromethyl)sulfonyl]pyrrole | 7 | 9 |
| 2-(p-Chlorophenyl)-5-[(trifluoromethyl)thio]pyrrole-3-carbonitrile | 0 | 3 |
| 2,3-Dibromo-5-p-tolyl-4-[(trifluoromethyl)sulfonyl]pyrrole | 5 | 7 |
| p-{2,3-Dibromo-4-[(trifluoromethyl)sulfonyl]pyrrol-2-yl}-benzonitrile | 9 | 5 |
| p-{5-Bromo-3-[(trifluoromethyl)sulfonyl]pyrrol-2-yl)}benzonitrile | 7 | 5 |
| 2,5-Dibromo-3-(p-chlorophenyl)-4-[(trifluoromethyl)sulfonyl]pyrrole | 5 | 5 |
| 2-Bromo-3-(p-chlorophenyl)-4-[(trifluoromethyl)sulfonyl]pyrrole | 7 | 9 |
| 3-(p-Chlorophenyl)-4-[(trifluoromethyl)sulfonyl]pyrrole | 9 | 7 |
| 2-(p-Chlorophenyl)-5-[(difluoromethyl)thio]pyrrole | 7 | 9 |
| 3,4-Dibromo-2-(p-chlorophenyl)-5-[(difluoromethyl)thio]pyrrole | 7 | 9 |
| 2,3-Dichloro-5-p-tolyl-4-[(trifluoromethyl)sulfonyl]pyrrole | 5 | 7 |
| 2,3-Dibromo-4-(p-chlorophenyl)-5-[(trifluoromethyl)sulfinyl]pyrrole | 7 | 9 |
| 2-(p-Chlorophenyl)-5-(trifluoro- | 0 | 9 |

TABLE II-continued

In Vitro Fungicidal Evaluations

| Compound | PYTHUL (25 ppm) | RHIZSO (25 ppm) |
|---|---|---|
| methyl)-3-[(trifluoromethyl)thio]pyrrole | | |
| 2-(p-Chlorophenyl)-5-(trifluoromethyl)-3-[(trifluoromethyl)sulfinyl]pyrrole | 0 | 5 |

What is claimed is:

1. A method for protecting plants from the effects of plant pathogenic fungi which comprises applying to the foliage of the plant, the seed of the plant or the soil in which the plant grows or is to be grown a fungicidally effective amount of a compound having the structural formula

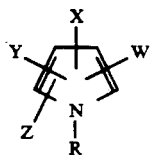

wherein
W is $S(O)_n CF_2 R_1$;
$R_1$ is H, F, Cl, Br, $CF_2H$, $CCl_2H$, $CClFH$, $CF_3$ or $CCl_3$;
n is an integer of 0, 1 or 2;
X is phenyl optionally substituted with one to three halogen, $C_1-C_3$ alkyl, $C_1-C_3$ alkoxy, $C_1-C_3$ alkylthio, $C_1-C_3$ alkylsulfinyl, $C_1-C_3$ alkylsulfonyl, CN, $NO_2$, $CF_3$, $R_2CF_2B$, $R_3CO$ or $NR_4R_5$ groups;
B is $S(O)_n$ or O;
$R_2$ is H, F, $CF_2H$, $CClFH$ or $CF_3$;
$R_3$ is $C_1-C_3$ alkyl, $C_1-C_3$ alkoxy or $NR_4R_5$;
$R_4$ is H or $C_1-C_3$ alkyl;
$R_5$ is H or $C_1-C_3$ alkyl or $R_6CO$;
$R_6$ is H or $C_1-C_3$ alkyl;
Y is H, halogen, $CF_3$, CN, $NO_2$, $S(O)_n CF_2 R_1$ or phenyl optionally substituted with one to three halogen, $C_1-C_3$ alkyl, $C_1-C_3$ alkoxy, $C_1-C_3$ alkylthio, $C_1-C_3$ alkylsulfinyl, $C_1-C_3$ alkylsulfonyl, CN, $NO_2$, $CF_3$, $R_2CF_2B$, $R_3Co$ or $NR_4R_5$ groups;
Z is H, halogen or $CF_3$;
R is H,

$C_1-C_6$ alkyl optionally substituted with one to three halogen atoms,
one tri($C_1-C_4$ alkyl)silyl,
one hydroxy,
one cyano,
one or two $C_1-C_4$ alkoxy groups optionally substituted with one to three halogen atoms,
one $C_1-C_4$ alkylthio,
one phenyl optionally substituted with one to three halogen atoms, one to three $C_1-C_4$ alkyl groups or one to three $C_1-C_4$ alkoxy groups,
one phenoxy group optionally substituted with one to three halogen atoms, one to three $C_1-C_4$ alkyl groups or one to three $C_1-C_4$ alkoxy groups,
one benzyloxy group optionally substituted on the phenyl ring with one to three halogen atoms, one to three $C_1-C_4$ alkyl groups or one to three $C_1-C_4$ alkoxy groups,
one $C_1-C_6$ alkylcarbonyloxy group optionally substituted with one to three halogen atoms,
one $C_2-C_6$ alkenylcarbonyloxy group optionally substituted with one to three halogen atoms,
one phenylcarbonyloxy group optionally substituted with one to three halogen atoms, one to three $C_1-C_4$ alkyl groups or one to three $C_1-C_4$ alkoxy groups,
one $C_1-C_6$ alkoxycarbonyl group optionally substituted with one to three halogen atoms or one to three $C_1-C_4$ alkoxy groups, or
one benzylcarbonyloxy group optionally substituted on the phenyl ring with one to three halogen atoms, one to three $C_1-C_4$ alkyl groups or one to three $C_1-C_4$ alkoxy groups,
$C_3-C_6$ alkenyl optionally substituted with one to three halogen atoms or one phenyl group, or
$C_3-C_6$ alkynyl optionally substituted with one to three halogen atoms or one phenyl group;
$R_8$ is hydrogen or $C_1-C_4$ alkyl;
$R_9$ is $C_1-C_6$ alkyl optionally substituted with one to three halogen atoms, or phenyl optionally substituted with one or two halogen, CN, $NO_2$, $C_1-C_4$ alkyl, $C_1-C_4$ alkoxy or $CF_3$ groups; Q is

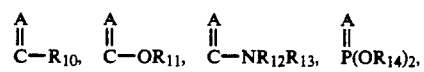

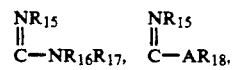

CN, $C_1-C_6$ alkyl optionally substituted with one or more phenyl, CN or halogen groups or phenyl optionally substituted with one to three $C_1-C_3$ alkyl, $C_1-C_3$ alkoxy, halogen, CN, $NO_2$, $CF_3$ or $NR_{21}R_{22}$ groups;
A is O or S;
$R_{10}$ is $C_1-C_6$ alkyl or phenyl;
$R_{11}$ is $C_1-C_6$ alkyl;
$R_{12}$ and $R_{13}$ are each independently hydrogen or $C_1-C_6$ alkyl;
$R_{14}$ is $C_1-C_4$ alkyl;
$R_{15}$ is hydrogen or $C_1-C_4$ alkyl;
$R_{16}$ and $R_{17}$ are each independently hydrogen or $C_1-C_4$ alkyl;
$R_{18}$ is $C_1-C_4$ alkyl; and
$R_{21}$ and $R_{22}$ are each independently hydrogen or $C_1-C_3$ alkyl.

2. The method according to claim 1 wherein the compound has the structural formula

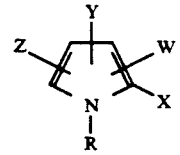

wherein
W is $S(O)_n CF_2 R_1$;
X is phenyl substituted with one to three halogen, CN, $NO_2$, $CF_3$ or $R_2CF_2B$ groups;
Y is H, Cl, Br, $CF_3$, CN or $S(O)_n CF_2 R_1$;
Z is H, Cl, Br or $CF_3$; and R is H or $C_1$-$C_4$ alkyl optionally substituted with one to three halogen atoms, one $C_1$-$C_4$ alkoxy group, one cyano, one $C_1$-$C_6$ alkylcarbonyloxy group, one phenylcarbonyloxy group optionally substituted with one to three halogen atoms or one $C_1$-$C_4$ alkyl group or one benzylcarbonyloxy group.

3. The method according to claim 2 wherein the compound has the structural formula

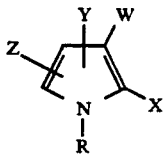

wherein
W is $SO_2CF_3$;
X is phenyl substituted with one or two halogen, $C_1$-$C_3$ alkyl or $CF_3$ groups;
Y is H, Cl, Br, $CF_3$ or CN;
Z is H, Cl or Br; and
R is H or $C_1$-$C_4$ alkyl substituted with one $C_1$-$C_4$ alkoxy group.

4. The method according to claim 2 wherein the compound has the structural formula

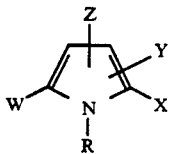

wherein
W is $SO_2CF_3$;
X is phenyl substituted with one or two halogen, $C_1$-$C_3$ alkyl or $CF_3$ groups;
Y is H, Cl, Br, $CF_3$, or CN;
Z is H, Cl, or Br; and
R is H, or $C_1C_4$ alkyl substituted with one $C_1$-$C_4$ alkoxy group.

5. The method according to claim 1 wherein the compound is applied to the foliage of the plants, seeds of the plants or soil in which they are growing or are to be grown at a rate of about 20 ppm to 1,000 ppm.

6. A method for the control or prevention of a disease caused by a phytopathogenic fungus which comprises contacting said fungus with a fungicidally effective amount of a compound having the structure

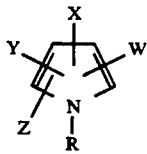

wherein
W is $S(O)_nCF_2R_1$;
$R_1$ is H, F, Cl, Br, $CF_2H$, $CCl_2H$, $CClFH$, $CF_3$ or $CCl_3$;
n is an integer of 0, 1 or 2;
X is phenyl optionally substituted with one to three halogen, $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, CN, $NO_2$, $CF_3$, $R_2CF_2B$, $R_3CO$ or $NR_4R_5$ groups;
B is $S(O)_n$ or O;

$R_2$ is H, F, $CF_2H$, $CClFH$ or $CF_3$;
$R_3$ is $C_1$-$C_3$ alkyl, $C_1$-$C_3$ alkoxy or $NR_4R_5$;
$R_4$ is H or $C_1$-$C_3$ alkyl;
$R_5$ is H or $C_1$-$C_3$ alkyl or $R_6CO$;
$R_6$ is H or $C_1$-$C_3$ alkyl;
Y is H, halogen, $CF_3$, CN, $NO_2$, $S(O)_nCF_2R_1$ or phenyl optionally substituted with one to three halogen, $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, CN, $NO_2$, $CF_3$, $R_2CF_2B$, $R_3Co$ or $NR_4R_5$ groups;
Z is H, halogen or $CF_3$;
R is H,

$C_1$-$C_6$ alkyl optionally substituted with one to three halogen atoms,
one tri($C_1$-$C_4$ alkyl)silyl,
one hydroxy,
one cyano,
one or two $C_1$-$C_4$ alkoxy groups optionally substituted with one to three halogen atoms,
one $C_1$-$C_4$ alkylthio,
one phenyl optionally substituted with one to three halogen atoms, one to three $C_1$-$C_4$ alkyl groups or one to three $C_1$-$C_4$ alkoxy groups,
one phenoxy group optionally substituted with one to three halogen atoms, one to three $C_1$-$C_4$ alkyl groups or one to three $C_1$-$C_4$ alkoxy groups,
one benzyloxy group optionally substituted on the phenyl ring with one to three halogen atoms, one to three $C_1$-$C_4$ alkyl groups or one to three $C_1$-$C_4$ alkoxy groups,
one $C_1$-$C_6$ alkylcarbonyloxy group optionally substituted with one to three halogen atoms,
one $C_2$-$C_6$ alkenylcarbonyloxy group optionally substituted with one to three halogen atoms,
one phenylcarbonyloxy group optionally substituted with one to three halogen atoms, one to three $C_1$-$C_4$ alkyl groups or one to three $C_1$-$C_4$ alkoxy groups,
one $C_1$-$C_6$ alkoxycarbonyl group optionally substituted with one to three halogen atoms or one to three $C_1$-$C_4$ alkoxy groups, or
one benzylcarbonyloxy group optionally substituted on the phenyl ring with one to three halogen atoms, one to three $C_1$-$C_4$ alkyl groups or one to three $C_1$-$C_4$ alkoxy groups,
$C_3$-$C_6$ alkenyl optionally substituted with one to three halogen atoms or one phenyl group, or
$C_3$-$C_6$ alkynyl optionally substituted with one to three halogen atoms or one phenyl group;
$R_8$ is hydrogen or $C_1$-$C_4$ alkyl;
$R_9$ is $C_1$-$C_6$ alkyl optionally substituted with one to three halogen atoms, or phenyl optionally substituted with one or two halogen, CN, $NO_2$, $C_1$-$C_4$ alkyl, $C_1$-$C_4$ alkoxy or $CF_3$ groups;

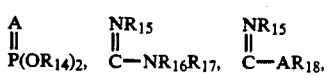

CN, $C_1$-$C_6$ alkyl optionally substituted with one or more phenyl, CN or halogen groups or phenyl optionally substituted with one to three $C_1$-$C_3$ alkyl, $C_1$-$C_3$ alkoxy, halogen, CN, $NO_2$, $CF_3$ or $NR_{21}R_{22}$ groups;

A is O or S;

$R_{10}$ is $C_1$-$C_6$ alkyl or phenyl;

$R_{11}$ is $C_1$-$C_6$ alkyl;

$R_{12}$ and $R_{13}$ are each independently hydrogen or $C_1$-$C_6$ alkyl;

$R_{14}$ is $C_1$-$C_4$ alkyl;

$R_{15}$ is hydrogen or $C_1$-$C_4$ alkyl;

$R_{16}$ and $R_{17}$ are each independently hydrogen or $C_1$-$C_4$ alkyl;

$R_{18}$ is $C_1$-$C_4$ alkyl; and $R_{21}$ and $R_{22}$ are each independently hydrogen or $C_1$-$C_3$ alkyl.

7. The method according to claim 6 wherein the compound has the structural formula

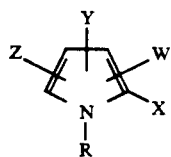

wherein

W is $S(O)_nCF_2R_1$;

X is phenyl substituted with one to three halogen, CN, $NO_2$, $CF_3$ or $R_2CF_2B$ groups;

Y is H, Cl, Br, $CF_3$, CN or $S(O)_nCF_2R_1$;

Z is H, Cl, Br or $CF_3$; and

R is H or $C_1$-$C_4$ alkyl optionally substituted with one to three halogen atoms, one $C_1$-$C_4$ alkoxy group, one cyano, one $C_1$-$C_6$ alkylcarbonyloxy group, one phenylcarbonyloxy group optionally substituted with one to three halogen atoms or one $C_1$-$C_4$ alkyl group or one benzylcarbonyloxy group.

8. The method according to claim 7 wherein the compound has the structural formula

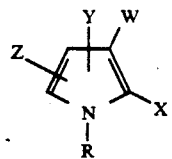

wherein

W is $SO_2CF_3$;

X is phenyl substituted with one to two halogen, $C_1$-$C_3$ alkyl or $CF_3$ groups;

Y is H, Cl, Br, $CF_3$ or CN;

Z is H, Cl or Br; and

R is H or $C_1$-$C_4$ alkyl substituted with one $C_1$-$C_4$ alkoxy group.

9. The method according to claim 8 wherein the compound has the structural formula

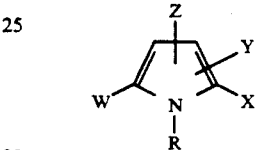

wherein

W is $SO_2CF_3$;

X is phenyl substituted with one or two halogen, $C_1$-$C_3$ alkyl or $CF_3$ groups;

Y is H, Cl, Br, $CF_3$, or CN;

Z is H, Cl, or Br; and

R is H, or $C_1$-$C_4$ alkyl substituted with one $C_1$-$C_4$ alkoxy group.

* * * * *